US012410114B2

(12) United States Patent
Sommerlade et al.

(10) Patent No.: US 12,410,114 B2
(45) Date of Patent: Sep. 9, 2025

(54) PROCESS FOR THE PREPARATION OF α-FUNCTIONALIZED KETONES

(71) Applicant: IGM GROUP B.V., Waalwijk (NL)

(72) Inventors: Reinhard Sommerlade, Neuenburg am Rhein (DE); Thomas Loerzer, Landau-Godramstrein (DE)

(73) Assignee: IGM GROUP B.V., Waalwijk (NL)

(*) Notice: Subject to any disclaimer, the term of this patent is extended or adjusted under 35 U.S.C. 154(b) by 467 days.

(21) Appl. No.: 16/603,533

(22) PCT Filed: Apr. 19, 2018

(86) PCT No.: PCT/EP2018/060012
§ 371 (c)(1),
(2) Date: Oct. 7, 2019

(87) PCT Pub. No.: WO2018/197325
PCT Pub. Date: Nov. 1, 2018

(65) Prior Publication Data
US 2020/0055806 A1 Feb. 20, 2020

(30) Foreign Application Priority Data
Apr. 24, 2017 (EP) .................................. 17167814

(51) Int. Cl.
*C07C 45/64* (2006.01)
*C07C 319/20* (2006.01)
*C07D 295/108* (2006.01)

(52) U.S. Cl.
CPC ............ *C07C 45/64* (2013.01); *C07C 319/20* (2013.01); *C07D 295/108* (2013.01); *C07C 2601/14* (2017.05); *C07C 2601/16* (2017.05); *C07C 2602/10* (2017.05)

(58) Field of Classification Search
CPC .... C07C 45/64; C07C 319/20; C07D 295/108
See application file for complete search history.

(56) References Cited

U.S. PATENT DOCUMENTS

| 4,318,791 | A | 3/1982 | Felder et al. |
| 4,496,447 | A | 1/1985 | Eichler et al. |
| 4,691,058 | A | 9/1987 | Stegmann |
| 4,740,624 | A | 4/1988 | Koehler et al. |
| 6,376,568 | B1 | 4/2002 | Baudin et al. |

FOREIGN PATENT DOCUMENTS

| DE | 2722264 | A1 | 11/1978 |
| EP | 0216884 | A | 4/1987 |
| EP | 0510754 | A1 | 10/1992 |
| EP | 1146033 | A2 | 10/2001 |
| FR | 1422701 | A | 12/1965 |
| FR | 2391183 | A1 | 12/1978 |
| JP | 54-99185 | A | 8/1979 |
| JP | 58-203934 | A | 11/1983 |
| JP | 61-236744 | A | 10/1986 |
| JP | 62-502403 | A | 9/1987 |
| JP | 63-254105 | A | 10/1988 |
| JP | 10-17630 | A | 1/1998 |
| JP | 10-60064 | A | 3/1998 |
| JP | 2008-514671 | A | 5/2008 |
| TW | 200616937 | A | 6/2006 |
| WO | 198605777 | A1 | 10/1986 |
| WO | 99/48963 | A2 | 9/1999 |
| WO | 02/36437 | A1 | 5/2002 |
| WO | 2004/099262 | A1 | 11/2004 |
| WO | 2006/034966 | A1 | 4/2006 |

OTHER PUBLICATIONS

Curphy et al. Tetrahedron Letters 41 (2000) 6977-6980.*
Majewski et al., Science of Synthesis, pp. 1011-1140, 2006.*
Applicant: IGM Group B.V.; "Process for the preparation of alpha-functionalized ketones"; Japanese Patent Application No. 2019-552906; Office Action; Oct. 27, 2020; 7 pgs.
Chen, et al., "An Efficient Method for the Synthesis of u-Hydroxyalkyl Aryl Ketones", Synthesis 2008, No. 20, 3205-3208.
Bang-Chi Chen, "a-Hydroxylation of Enolates and Silyl Enol Ethers", Organic Reactions, vol. 62, 2003.
Jain, et al., "Synthesis of Isopentenylated 4-Hydroxy-3-Methoxycoumarins and W-Methyl-W-Desacetyl Ripariochromene-B", pp. 14-166, 1976.
Davis, et al., "Oxidation of Silyl Enol Ethers Using 2-Sulfonyloxaziridines. Synthesis of a-Siloxy Epoxides and a-Hydroxy Carbonyl Compounds", J. Org. Chen., 1987, 52, 954-955.
Chuang, et al., "A Dinuclear Palladium Catalyst for r-Hydroxylation of Carbonyls with O2", JACS, 1760-1760, 2011.
Aneja, et al., "Synthesis of Benzo_Furan Derivatives-I", Tetrahedron, 1958, vol. 2, pp. 203-210.
Koporowski, et al., "Asymmetric oxidation of enol phosphates to a-hydroxy ketones by (salen)manganese(III) complex. Effects of the substitution pattern of enol phosphates on the stereochemistry of oxygen transfer", Tetrahedron 62 (2006) 12363-12374.
Liang, et al., "12- or NBS-Catalyzed Highly Efficient a-Hydroxylation of Ketones with Dimethyl Sulfoxide", Org. Lett. 2015, 17, 876-879.
Liang, et al., "Highly Efficient COH Hydroxylation of Carbonyl Compounds with Oxygen under Mild Conditions", Angew. Chem. 2014, 126, 558-562.
Taiwan Application No. 107113295; Filed Apr. 19, 2018; Taiwan Office Action; Mar. 11, 2019; 19 pgs.
Applicant: IGM Malta Limited; "Process for the Preparation of Alpha-Functionalized Ketones"; European Patent Application No. 17167814.7; Partial European Search Report; Sep. 28, 2017; 16 pgs.
Taiwan Search Report; Taiwan Application No. 10820220710; dated Mar. 13, 2019; 2 pgs.

* cited by examiner (Continued)

Primary Examiner — Rebecca L Anderson
(74) Attorney, Agent, or Firm — Tarolli, Sundheim, Covell & Tummino LLP

(57) ABSTRACT

The present invention refers to a process for the preparation of an α-functionalized ketone, an α-functionalized ketone obtained by the process, a photopolymerizable composition comprising the α-functionalized ketone and at least one photopolymerizable unsaturated compound, a method of preparing an article, an article obtained by the method, as well as the use of the α-functionalized ketone or the photopolymerizable composition as photoinitiator.

19 Claims, No Drawings

PROCESS FOR THE PREPARATION OF α-FUNCTIONALIZED KETONES

FIELD OF THE INVENTION

The present invention refers to a process for the preparation of an α-functionalized ketone, an α-functionalized ketone obtained by said process, a photopolymerizable composition comprising the α-functionalized ketone and at least one photopolymerizable unsaturated compound, a method of preparing an article, an article obtained by said method, as well as the use of the α-functionalized ketone or the photopolymerizable composition as photoinitiator.

BACKGROUND OF THE INVENTION

Photopolymerization processes have attained major importance in a large number of applications, for example in overprint coatings, printing inks, in the manufacture of electronic printed circuit boards and printing plates, and in the coating of various substrates, such as wood, plastics, paper, glass or metal, due their tremendous advantages over conventional hardening systems. One advantage of photo-curing by UV irradiation in the presence of photoinitiators is the great speed. However, the speed is heavily dependent on the photoinitiator used. Among the most effective photoinitiators are α-hydroxylated ketones as described e.g. in German Patent No. 2,722,264 and US patent application U.S. Pat. No. 4,740,624. Further methods for the α-functionalization of ketones are described e.g. in Gary Jing Chuang et al., "A Dinuclear Palladium Catalyst for α-Hydroxylation of Carbonyls with $O_2$", J. Am. Chem. Soc. 133, 1760-1762 (2011). Chengqun Chen et al. "An Efficient Method for the Synthesis of α-Hydroxyalkyl Aryl Ketones", Synthesis 2008, No. 20, 3205-3208; Marek Koprowski et al., "Asymmetric oxidation of enol phosphates to α-hydroxy ketones by (salen)manganese(III) complex; Effects of the substitution pattern of enol phosphates on the stereochemistry of oxygen transfer", Tetrahedron 62 12363-12374 (2006); Franklin A. Davis et al., "Oxidation of Silyl Enol Ethers Using 2-Sulfonyloxaziridines; Synthesis of α-Siloxy Epoxides and α-Hydroxy Carbonyl Compounds", J. Org. Chem. 52, 954-955 (1987); Yu-Feng Liang et al., "Highly Efficient C—H Hydroxylation of Carbonyl Compounds with Oxygen under Mild Conditions", Angew. Chem. 2014, 126, 558-562; Yu-Feng Liang et al., "$I_2$- or NBS-Catalyzed Highly Efficient αHydroxylation of Ketones with Dimethyl Sulfoxide", Org. Lett. 17, 876-879 (2015); Bang-Chi Chen et al., "α-hydroxylation of enolates and silyl enol ethers", Organic Reactions, Vol. 62, 2003, published by John Wiley & Sons, Inc.

However, the processes used for the preparation of the α-hydroxylated ketones have a number of disadvantages. In particular, it is to be noted that the α-hydroxylated ketones are prepared by multiple step reactions resulting in a great variety of by-products which reduce the yield and purity of the desired α-hydroxylated ketone. Furthermore, elaborate purification steps are required. Accordingly, the well-known processes of the prior art are quite complex, require costly chemicals or catalysts as well as are time- and chemical-consuming.

Despite of numerous efforts, a simple and cheap process for this kind of functionalization is still missing. Therefore, there is a continuous need in the art for providing a process for the preparation of α-functionalized ketones avoiding the forgoing disadvantages. In particular, it is desirable to provide a process for the preparation of α-functionalized ketones which avoids a multiple step reaction. Furthermore, it is desirable to provide a process for the preparation of α-functionalized ketones using cheap and safe starting materials. Furthermore, it is desirable to provide a process for the preparation of α-functionalized ketones which avoids elaborate purification steps for obtaining the desired α-functionalized ketones. In addition thereto, it is desirable to provide a process for the preparation of α-functionalized ketones which avoids the formation of excessive by-products and thus increases the yield and purity of the desired α-functionalized ketones. Furthermore, there is still a need for a process which allows the preparation of α-functionalized ketones that have not been accessible by the processes of the prior art up to now.

Accordingly, it is an object of the present invention to provide a process for the preparation of α-functionalized ketones. Furthermore, it is an object of the present invention to provide a one-pot process for the preparation of α-functionalized ketones. It is an even further object of the present invention to provide a process for the preparation of α-functionalized ketones using cheap starting materials and without elaborate purification steps for obtaining the desired α-functionalized ketones. It is an even further object of the present invention to provide a process for the preparation of α-functionalized ketones which increases the yield and purity of the desired α-functionalized ketones. It is another object of the present invention to provide a process which allows the preparation of α-functionalized ketones that have not been accessible by the processes of the prior art up to now. It is a further object of the present invention to provide new α-functionalized ketones that can be used as photoinitiators.

SUMMARY OF THE INVENTION

The foregoing and other objects are solved by the subject-matter of the present invention.

According to a first aspect of the present invention, a process for the preparation of an α-functionalized ketone of the general formula I is provided,

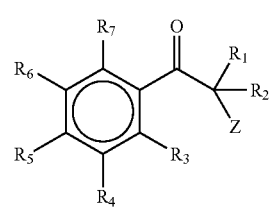

I wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_6$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{16}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{16}$-alkenylarylalkoxy or $R_8$ form a $C_3$-$C_9$-alicyclic system together with the connecting N atom, optionally one or more carbon atoms are replaced with O, or two adjacent R form an aromatic system together with the benzene ring of formula I;

Z is selected from $OR_9$, $NHR_9$ and $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O;

characterized in that a ketone of the general formula II

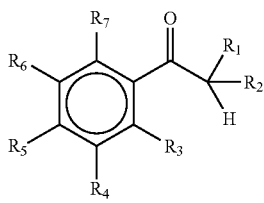

wherein $R_1$, $R_2$, $R_3$, $R_4$, $R_5$, $R_6$ and $R_7$ are as defined above, is contacted under phase-transfer conditions with an at least partially halogenated $C_2$-$C_8$-alkane and/or $C_2$-$C_8$-alkene, and a base selected from the group comprising alkali metal hydroxide, earth alkali metal hydroxide, alkali metal $C_1$-$C_8$-alkoxide, earth alkali metal $C_1$-$C_8$-alkoxide and mixtures thereof, or a base selected from the group comprising alkali metal hydroxide, earth alkali metal hydroxide, alkali metal $C_1$-$C_8$-alkoxide, earth alkali metal $C_1$-$C_8$-alkoxide and mixtures thereof together with the protonated form of Z as defined above.

The inventors surprisingly found out that such a process is suitable for the preparation of α-functionalized ketones in a one-pot process by using cheap starting materials and avoiding elaborate purification steps for obtaining the desired α-functionalized ketones. The process for the preparation of α-functionalized ketones thus increases the yield and purity of the desired α-functionalized ketones. Furthermore, the process allows the preparation of α-functionalized ketones that have not been accessible by the processes of the prior art up to now and thus also results in new α-functionalized ketones that can be used as photoinitiators.

Advantageous embodiments of the inventive process are defined in the corresponding sub-claims.

According to one embodiment, $R_1$ and $R_2$ are the same.

According to another embodiment, $R_1$ and $R_2$ are selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to yet another embodiment, $R_1$ and $R_2$ are different and are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to one embodiment, $R_1$ and $R_2$ form $C_4$-$C_{10}$-cycloalkyl, preferably $C_4$-$C_8$-cycloalkyl, and most preferably $C_6$-cycloalkyl, together with the connecting C atom.

According to another embodiment, that $R_3$, $R_4$, $R_5$, $R_6$ and $R_7$ are the same.

According to yet another embodiment, $R_3$, $R_4$, $R_5$, $R_6$ and $R_7$ are selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to one embodiment, $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy; $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

According to another embodiment, one of $R_3$, $R_4$, $R_5$, $R_6$ and $R_7$ is linear or branched $C_2$-$C_8$-alkenyl, preferably $C_2$-$C_6$-alkenyl and most preferably $C_2$-$C_3$-alkenyl; $C_1$-$C_8$-alkoxy, preferably $C_1$-$C_6$-alkoxy and most preferably $C_1$-$C_3$-alkoxy; $C_2$-$C_8$-alkenyloxy, preferably $C_2$-$C_6$-alkenyloxy and most preferably $C_3$-$C_5$-alkenyloxy; $C_9$-$C_{15}$-alkenylarylalkoxy, preferably $C_9$-$C_{12}$-alkenylarylalkoxy and most preferably $C_9$-$C_{10}$-alkenylarylalkoxy; or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to ye another embodiment, two or three of $R_3$, $R_4$, $R_5$, $R_6$ and $R_7$ are linear or branched $C_2$-$C_8$-alkenyl, preferably $C_2$-$C_6$-alkenyl and most preferably $C_2$-$C_3$-alkenyl; $C_1$-$C_8$-alkoxy, preferably $C_1$-$C_6$-alkoxy and most preferably $C_1$-$C_3$-alkoxy; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to one embodiment, that $R_3$ and $R_4$ or $R_4$ and $R_5$ form an aromatic system together with the benzene ring of formula I, preferably a bicyclic, tricyclic or tetracyclic aromatic system, more preferably an aromatic system selected from a naphthyl, anthracenyl and phenanthrenyl system.

According to another embodiment, one of the remaining R is linear or branched $C_2$-$C_8$-alkenyl, preferably $C_2$-$C_6$-alkenyl and most preferably $C_2$-$C_3$-alkenyl; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to yet another embodiment, Z is $OR_9$ with $R_9$ being selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy and $C_9$-$C_{15}$-alkenylarylalkoxy, preferably $R_9$ is H or Z is $NR_{10}R_{11}$ with $R_{10}$ and $R_{11}$ being independently selected from H, linear or branched $C_1$-$C_8$-alkyl, $C_3$-$C_8$-cycloalkyl, $C_6$-$C_{14}$-aryl, or $R_{10}$ and $R_{11}$ form a $C_3$-$C_6$-alicyclic system together with the connecting N atom, optionally one or more carbon atoms are replaced with O, preferably $R_{10}$ and $R_{11}$ form a $C_5$-$C_6$-alicyclic system together with the connecting N atom and one or more carbon atoms are replaced with O.

According to one embodiment, the at least partially halogenated $C_2$-$C_8$-alkane and/or $C_2$-$C_8$-alkene is fully halogenated, preferably the at least partially halogenated $C_2$-$C_8$-alkane and/or $C_2$-$C_8$-alkene is selected from hexachloroethane, tetrachoroethylene and mixtures thereof.

According to another embodiment, the base is selected from the group comprising sodium hydroxide; lithium hydroxide; potassium hydroxide; sodium $C_1$-$C_6$-alkoxide, preferably sodium $C_1$-$C_4$-alkoxide and most preferably sodium $C_1$-$C_2$-alkoxide; lithium $C_1$-$C_6$-alkoxide, preferably lithium $C_1$-$C_4$-alkoxide and most preferably lithium $C_1$-$C_2$-alkoxide; potassium $C_1$-$C_6$-alkoxide, preferably potassium $C_1$-$C_4$-alkoxide and most preferably potassium $C_1$-$C_2$-alkoxide; and mixtures thereof; or the base is selected from sodium $C_1$-$C_6$-alkoxide, preferably sodium $C_1$-$C_4$-alkoxide and most preferably sodium $C_1$-$C_2$-alkoxide; potassium $C_1$-$C_6$-alkoxide, preferably potassium $C_1$-$C_4$-alkoxide and most preferably potassium $C_1$-$C_2$-alkoxide, together with the protonated form of Z as defined above.

According to yet another embodiment, the base is in form of an aqueous solution or the base is provided in an organic solvent, preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3-dioxane or 1,4-dioxane, 1,2-dimethoxyethane, diethyleneglycol dimethyl ether, triethyleneglycol dimethyl ether and mixtures thereof.

According to one embodiment, the process is carried out at a temperature of at least 30° C., preferably in the range from 30 to 120° C., more preferably in the range from 40 to 100° C., and most preferably in the range from 40 to 90° C.

According to another embodiment, the process is carried out in an organic solvent, preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3-dioxane or 1,4-dioxane, 1,2-dimethoxyethane, diethyleneglycol dimethyl ether, triethyleneglycol dimethyl ether and mixtures thereof.

According to yet another embodiment, the process is carried out in the presence of a phase-transfer catalyst, preferably the phase-transfer catalyst is selected from a quaternary ammonium salt, tetraalkylphosphonium chloride, tetraalkylphosphonium bromide and mixtures thereof, preferably the phase-transfer catalyst is a tetraalkylammonium salt or a trialkylarylammonium salt, more preferably the phase-transfer catalyst is selected from the group comprising benzyltrimethylammonium hydroxide, benzyltriethylammonium chloride, tetrabutylammonium chloride, tetrabutylammonium bromide, tetrabutylammonium hydrogensulfate, tetrabutylammonium hydroxide, methyltrioctylammonium chloride, cetyl pyridinium and mixtures thereof.

According to one embodiment, the α-functionalized ketone is obtained in an one-pot reaction.

According to another embodiment, the process further comprises a step of i) separating the obtained organic and aqueous phases, and/or ii) extracting the obtained aqueous phase with the organic solvent used in the process and combining the obtained organic phases, and/or iii) acidifying the obtained organic phase to a pH of 3 to 6.5.

According to a further aspect of the present invention, an α-functionalized ketone obtained by a process, as defined herein, is provided.

According to another aspect of the present invention, an α-functionalized ketone as defined herein, is provided, with the proviso that at least one of $R_3$, $R_4$, $R_5$, $R_6$ and $R_7$ is linear or branched $C_2$-$C_8$-alkenyl, preferably $C_2$-$C_6$-alkenyl and most preferably $C_2$-$C_3$-alkenyl, $C_2$-$C_8$-alkenyloxy, preferably $C_2$-$C_6$-alkenyloxy and most preferably $C_3$-$C_5$-alkenyloxy, and $C_9$-$C_{15}$-alkenylarylalkoxy, preferably $C_9$-$C_{12}$-alkenylarylalkoxy and most preferably $C_9$-$C_{10}$-alkenylarylalkoxy.

According to a further aspect of the present invention, a photopolymerizable composition comprising the α-functionalized ketone, as defined herein, and at least one photopolymerizable unsaturated compound is provided.

According to a still further aspect of the present invention, a method of preparing an article is provided. The method comprising the steps of:

a) preparing a coating and/or ink composition comprising the α-functionalized ketone as defined herein or the photopolymerizable composition comprising an α-functionalized ketone as defined herein, b) applying the coating and/or ink composition at least partially on at least one surface of an article, and c) curing the coating and/or ink composition by means of ultra-violet radiation.

According to an even further aspect, an article obtained by a method of preparing an article as defined herein is provided. It is preferred that the article is a packaging article, more preferably a food or beverage packaging article, an article of flooring or an article of furniture.

According to another aspect, the use of the α-functionalized ketone as defined herein or the photopolymerizable composition as defined herein as photoinitiator is provided. It is preferred that the α-functionalized ketone as defined herein or the photopolymerizable composition as defined herein is used as photoinitiator in a method of preparing an article or as photoinitiator in an article, preferably a packaging article, more preferably a food or beverage packaging article, an article of flooring or an article of furniture.

In the following, the details and preferred embodiments of the inventive process for the preparation of an α-functionalized ketone will be described in more detail. It is to be understood that these technical details and embodiments also apply to the inventive products, methods and uses, as far as applicable.

DETAILED DESCRIPTION OF THE INVENTION

A process for the preparation of an α-functionalized ketone is provided. It is appreciated that an α-functionalized ketone of the general formula I is prepared,

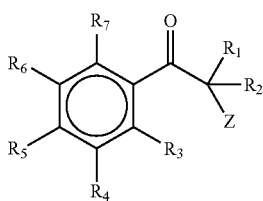

wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy or $R_8$ form a $C_3$-$C_9$-alicyclic system together with the connecting N atom, optionally one or more carbon atoms are replaced with O, or two adjacent R form an aromatic system together with the benzene ring of formula I;

Z is selected from $OR_9$, $NHR_9$ and $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

As regards $R_1$ and $R_2$ in the general formula I, it is to be noted that they can be the same or different. Preferably, $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom.

The term "linear or branched $C_1$-$C_8$-alkyl" in the meaning of the present invention refers to a linear or branched chain alkyl group having 1 to 8 carbon atoms, and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl and 1,1,3,3-tetramethylbutyl.

The term "$C_3$-$C_8$-cycloalkyl" in the meaning of the present invention refers to a cyclic alkyl having 3 to 8 carbon atoms, and includes, for example, cyclopropyl, cyclobutyl, cyclopentyl, cyclohexyl, and cycloheptyl.

The term "$C_5$-$C_8$-cycloalkenyl" in the meaning of the present invention refers to a cyclic alkenyl having 3 to 8 carbon atoms, and includes, for example, cyclopentenyl, cyclohexenyl, and cycloheptenyl.

The term "linear or branched $C_2$-$C_8$-alkenyl" in the meaning of the present invention refers to a linear or branched chain alkenyl group having 2 to 8 carbon atoms, and includes, for example, ethenyl, propenyl such as 2-propenyl, butenyl, triisobutenyl, pentenyl, hexenyl, heptenyl and octenyl. The term "alkenyl" in the meaning of the present invention includes the cis and trans isomers.

The term "linear or branched $C_2$-$C_8$-alkynyl" in the meaning of the present invention refers to a linear or branched chain alkynyl group having 2 to 8 carbon atoms, and includes, for example, ethynyl, propynyl such as 1-propynyl or 2-propynyl, e.g. propargyl, butynyl, pentynyl, hexynyl, heptynyl and octynyl.

The term "$C_6$-$C_{14}$-aryl" in the meaning of the present invention refers to a group containing one or more 6-membered unsaturated hydrocarbon ring(s), wherein the unsaturation is represented formally by conjugated double bonds and which may optionally be substituted at one or more carbon atoms of such ring(s) by independently selected alkyl groups. Thus, the term "$C_6$-$C_{14}$-aryl" preferably includes (unsubstituted) $C_6$-$C_{10}$-aryl and $C_6$-$C_{14}$-alkylaryl. Suitable examples include, for example, phenyl, naphthyl, methylphenyl, dimethoxyphenyl, 5-isopropyl-2-methylphenyl, methylphenyl, ethylphenyl, dimethylphenyl, t-butylphenyl, methylnaphthyl and dimethylnaphthyl.

The term "form $C_3$-$C_{12}$-cycloalkyl together with the connecting C atom" in the meaning of the present invention refers to a mono-, bi- or tricyclic alkyl having 3 to 12 carbon atoms, and includes, for example, cyclopropyl, cyclobutyl, cyclopentyl, cyclohexyl, cycloheptyl, norbornyl and adamantyl.

The term "form $C_5$-$C_{12}$-cycloalkenyl together with the connecting C atom" in the meaning of the present invention refers to a mono-, bi- or tricyclic alkenyl having 5 to 12 carbon atoms, and includes, one or more, preferably one, double bond(s). Suitable examples include, for example, cyclopentenyl, cyclohexenyl, cyclohexadienyl and cycloheptenyl. It is appreciated that the double bond of the $C_5$-$C_{12}$-cycloalkenyl is located such that an α,β-unsaturated carbonyl compound is not formed. Thus, $R_1$ and $R_2$ in the general formula I can form $C_5$-$C_{12}$-cycloalkenyl together with the connecting C atom with the proviso that no α,β-unsaturated carbonyl compound is formed.

In one embodiment, $R_1$ and $R_2$ are the same or different and are independently selected from H, linear or branched $C_1$-$C_8$-alkyl, $C_3$-$C_8$-cycloalkyl, or form $C_3$-$C_{12}$-cycloalkyl together with the connecting C atom. Preferably, $R_1$ and $R_2$ are the same or different and are independently selected from H or linear or branched $C_1$-$C_8$-alkyl.

For example, $R_1$ and $R_2$ are the same. In this embodiment, $R_1$ and $R_2$ are preferably selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom.

In one embodiment, $R_1$ and $R_2$ are the same and are H.

In another embodiment, $R_1$ and $R_2$ are the same and are linear or branched $C_1$-$C_8$-alkyl, e.g. linear $C_1$-$C_8$-alkyl. For example, $R_1$ and $R_2$ are the same and are linear or branched $C_1$-$C_6$-alkyl, e.g. linear $C_1$-$C_6$-alkyl, preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl. It is especially preferred that $R_1$ and $R_2$ are the same and are $C_1$- or $C_2$-alkyl, e.g. $C_1$-alkyl.

In another embodiment, $R_1$ and $R_2$ form $C_3$-$C_{12}$-cycloalkyl together with the connecting C atom. For example, $R_1$ and $R_2$ form $C_4$-$C_{10}$-cycloalkyl, preferably $C_4$-$C_8$-cycloalkyl, even more preferably $C_4$-$C_6$-cycloalkyl, and most preferably $C_5$- or $C_6$-cycloalkyl, e.g. $C_6$-cycloalkyl, together with the connecting C atom.

In another embodiment, $R_1$ and $R_2$ are the same and are linear or branched $C_2$-$C_8$-alkenyl, e.g. linear $C_2$-$C_8$-alkenyl. For example, $R_1$ and $R_2$ are the same and are linear or branched $C_2$-$C_6$-alkenyl, e.g. linear $C_2$-$C_6$-alkenyl, preferably linear or branched $C_2$-$C_4$-alkenyl, e.g. linear $C_2$-$C_4$-alkenyl, and most preferably linear or branched $C_2$- or $C_3$-alkenyl, e.g. linear $C_2$- or $C_3$-alkenyl. It is especially preferred that $R_1$ and $R_2$ are the same and are $C_3$-alkenyl.

In another embodiment, $R_1$ and $R_2$ are the same and are linear or branched $C_2$-$C_8$-alkynyl, e.g. linear $C_2$-$C_8$-alkynyl. For example, $R_1$ and $R_2$ are the same and are linear or branched $C_2$-$C_6$-alkynyl, e.g. linear $C_2$-$C_6$-alkynyl, preferably linear or branched $C_2$-$C_4$-alkynyl, e.g. linear $C_2$-$C_4$-alkynyl, and most preferably linear or branched $C_2$- or $C_3$-alkynyl, e.g. linear $C_2$- or $C_3$-alkynyl. It is especially preferred that $R_1$ and $R_2$ are the same and are $C_3$-alkynyl.

In another embodiment, $R_1$ and $R_2$ are the same and are linear or branched $C_6$-$C_{14}$-aryl, e.g. (unsubstituted) $C_6$-$C_{10}$-aryl or $C_6$-$C_{14}$-alkylaryl. For example, $R_1$ and $R_2$ are the same and are (unsubstituted) $C_6$- or $C_{10}$-aryl. Alternatively, $R_1$ and $R_2$ are the same and are $C_8$-$C_{12}$-alkylaryl.

In another embodiment, $R_1$ and $R_2$ form $C_5$-$C_{12}$-cycloalkenyl together with the connecting C atom. For example, $R_1$ and $R_2$ form $C_5$-$C_{10}$-cycloalkenyl, preferably $C_5$-$C_8$-cycloalkenyl and most preferably $C_5$- or $C_6$-cycloalkenyl, e.g. $C_6$-cycloalkenyl, together with the connecting C atom.

If $R_1$ and $R_2$ are the same, it is preferred that $R_1$ and $R_2$ are linear or branched $C_1$-$C_8$-alkyl, preferably linear $C_1$-$C_8$-alkyl, or form $C_3$-$C_{12}$-cycloalkyl, preferably $C_5$- or $C_6$-cycloalkyl, together with the connecting C atom. More preferably, $R_1$ and $R_2$ are linear or branched $C_1$-$C_8$-alkyl, preferably linear $C_1$-$C_8$-alkyl, or form $C_3$-$C_{12}$-cycloalkyl. Most preferably, $R_1$ and $R_2$ are linear or branched $C_1$-$C_8$-alkyl, preferably linear $C_1$-$C_8$-alkyl. Alternatively, $R_1$ and $R_2$ are different. In this embodiment, $R_1$ and $R_2$ are preferably independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl or $C_6$-$C_{14}$-aryl. For example, $R_1$ and $R_2$ are different and are selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, more preferably linear or branched $C_2$-$C_4$-alkenyl, e.g. linear $C_2$-$C_4$-alkenyl, even more preferably linear or branched $C_2$- or $C_3$-alkenyl, e.g. linear $C_2$- or $C_3$-alkenyl and most preferably $C_3$-alkenyl, and linear or branched $C_2$-$C_8$-alkynyl, e.g. linear $C_2$-$C_8$-alkynyl, preferably linear or branched $C_2$-$C_6$-alkynyl, e.g. linear $C_2$-$C_6$-alkynyl, more preferably linear or branched $C_2$-$C_4$-alkynyl, e.g. linear $C_2$-$C_4$-alkynyl, even more preferably linear or branched $C_2$- or $C_3$-alkynyl, e.g. linear $C_2$- or $C_3$-alkynyl and most preferably $C_3$-alkynyl, e.g. propargyl. In one embodiment, $R_1$ and $R_2$ are different and are selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl. In one embodiment, $R_1$ and $R_2$ are different and are selected from H and $C_1$- or $C_2$-alkyl, preferably $C_2$-alkyl.

If $R_1$ and $R_2$ are different, $R_1$ or $R_2$ is preferably H and the remaining $R_1$ or $R_2$ is preferably linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, even more preferably linear $C_1$-$C_3$-alkyl, and most preferably $C_1$- or $C_2$-alkyl, e.g. $C_2$-alkyl.

Preferably, $R_1$ and $R_2$ are the same.

The α-functionalized ketone of the general formula I further comprises residues $R_3$, $R_4$, $R_5$, $R_6$ and $R_7$. It is appreciated that $R_3$, $R_4$, $R_5$, $R_6$ and $R_7$ can be the same or different. Furthermore, $R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, or $R_8$ form a $C_3$-$C_9$-alicyclic system together with the connecting N atom, optionally one or more carbon atoms are replaced with O, or two adjacent R form an aromatic system together with the benzene ring of formula I.

The term "$C_1$-$C_8$-alkoxy" in the meaning of the present invention means that the alkoxy moiety has a linear or branched chain alkyl having 1 to 8 carbon atoms, and includes, for example, methoxy, ethoxy, propoxy, isopropoxy, butoxy, isobutoxy, tertiary butoxy, pentyloxy, hexyloxy, heptyloxy and octyloxy.

The term "$C_2$-$C_8$-alkenyloxy" in the meaning of the present invention means that the alkenyloxy moiety has a linear or branched chain alkenyl having 2 to 8 carbon atoms, and includes, for example, ethenyloxy, propenyloxy, butenyloxy, triisobutenyloxy, pentenyloxy, hexenyloxy, heptenyloxy and octenyloxy.

The term "$C_3$-$C_8$-cycloalkoxy" in the meaning of the present invention means that the cycloalkoxy moiety has a cyclic alkyl having 3 to 8 carbon atoms, and includes, for example, cyclopropyloxy, cyclobutyloxy, cyclopentyloxy, cyclohexyloxy, and cycloheptyloxy.

The term "$C_7$-$C_{15}$-arylalkoxy" in the meaning of the present invention means that the alkoxy moiety has a linear or branched chain alkyl having 1 to 8 carbon atoms, preferably 1 or 2 carbon atoms, which is connected to $C_6$-$C_{14}$-aryl.

The term "$C_7$-$C_{15}$-arylalkyl" in the meaning of the present invention means that the alkyl moiety is a linear or branched chain alkyl having 1 to 4 carbon atoms, preferably 1 or 2 carbon atoms, which is connected to $C_6$-$C_{14}$-aryl.

The term "$C_9$-$C_{15}$-alkenylarylalkoxy" in the meaning of the present invention means that the alkoxy moiety has a linear or branched chain alkyl having 1 to 8 carbon atoms, preferably 1 or 2 carbon atoms, which is connected to $C_6$-$C_{14}$-aryl, preferably $C_6$-aryl, which is further connected to linear or branched $C_2$-$C_8$-alkenyl, preferably $C_2$-alkenyl. Preferably, the alkoxy and alkenyl moieties are connected in para-position of the aryl moiety.

In one embodiment, $R_3$, $R_4$, $R_5$, $R_6$ and $R_7$ are the same. In this embodiment, $R_3$, $R_4$, $R_5$, $R_6$ and $R_7$ are the same and are selected from H and linear or branched $C_1$-$C_8$-alkyl, e.g. linear $C_1$-$C_8$-alkyl. For example, $R_3$, $R_4$, $R_5$, $R_6$ and $R_7$ are the same and are linear or branched $C_1$-$C_6$-alkyl, e.g. linear $C_1$-$C_6$-alkyl, preferably linear or branched $C_1$-$C_4$-alkyl, e.g. linear $C_1$-$C_4$-alkyl, and most preferably linear $C_1$-$C_3$-alkyl, e.g. linear $C_1$- or $C_2$-alkyl. It is especially preferred that $R_3$, $R_4$, $R_5$, $R_6$ and $R_7$ are the same and are H.

Alternatively, $R_3$, $R_4$, $R_5$, $R_6$ and $R_7$ are different. In this embodiment, $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

The term "at least one" in the meaning of the present invention means that one or more of $R_3$, $R_4$, $R_5$, $R_6$ and $R_7$ is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-Cis-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

For example, one or two or three of $R_3$, $R_4$, $R_5$, $R_6$ and $R_7$ is/are selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom. For example, one or two of $R_3$, $R_4$, $R_5$, $R_6$ and $R_7$ is/are selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

Preferably, one of $R_3$, $R_4$, $R_5$, $R_6$ and $R_7$ is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

If $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom, it is preferred that the remaining ones are selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl. For example, $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom and the remaining ones are H.

In one embodiment, $R_3$, $R_4$, $R_5$, $R_6$ and $R_7$ are different and one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

For example, $R_3$, $R_4$, $R_5$, $R_6$ and $R_7$ are different and one of them is linear or branched $C_2$-$C_8$-alkenyl, e.g. linear $C_2$-$C_8$-alkenyl; preferably linear or branched $C_2$-$C_6$-alkenyl, e.g. linear $C_2$-$C_6$-alkenyl; and most preferably $C_2$-$C_3$-alkenyl, e.g. $C_2$- or $C_3$-alkenyl; and the remaining ones are H.

Alternatively, $R_3$, $R_4$, $R_5$, $R_6$ and $R_7$ are different and one of them is $C_2$-$C_8$-alkenyloxy, preferably $C_2$-$C_6$-alkenyloxy and most preferably $C_3$-$C_6$-alkenyloxy, e.g. $C_3$- or $C_4$-alkenyloxy, especially $C_3$-alkenyloxy; and the remaining ones are H.

In one embodiment, $R_3$, $R_4$, $R_5$, $R_6$ and $R_7$ are different and one of them is $C_2$-$C_8$-alkenyloxy, preferably $C_2$-$C_6$-alkenyloxy and most preferably $C_3$-$C_6$-alkenyloxy, e.g. $C_3$- or $C_4$-alkenyloxy, especially $C_3$-alkenyloxy; and the remaining ones are independently selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl.

For example, $R_3$, $R_4$, $R_5$, $R_6$ and $R_7$ are different and one of them is $C_2$-$C_8$-alkenyloxy, preferably $C_2$-$C_6$-alkenyloxy and most preferably $C_3$-$C_6$-alkenyloxy, e.g. $C_3$- or $C_4$-alkenyloxy, especially $C_3$-alkenyloxy; and two of the remaining ones are H and two of the remaining ones are linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl.

Alternatively, $R_3$, $R_4$, $R_5$, $R_6$ and $R_7$ are different and one of them is $C_9$-$C_{16}$-alkenylarylalkoxy, preferably $C_9$-$C_{12}$-alkenylarylalkoxy and most preferably $C_9$-$C_{10}$-alkenylarylalkoxy; and the remaining ones are H.

Alternatively, $R_3$, $R_4$, $R_5$, $R_6$ and $R_7$ are different and one of them is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H.

Alternatively, $R_3$, $R_4$, $R_5$, $R_6$ and $R_7$ are different and one of them is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_6$- or $C_6$-alicyclic system, together with the connecting N atom; and the remaining ones are H. Optionally one or more carbon atoms are replaced with O. Preferably, $R_3$, $R_4$, $R_5$, $R_6$ and $R_7$ are different and one of them is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_5$- or $C_6$-alicyclic system, together with the connecting N atom, wherein one or more, preferably one, carbon atoms are replaced with O; and the remaining ones are H.

If $R_3$, $R_4$, $R_5$, $R_6$ and $R_7$ are different and one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom, it is preferred that $R_5$ is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

Thus, if $R_3$, $R_4$, $R_5$, $R_6$ and $R_7$ are different and one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-Cis-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom, it is preferred that this group is in para-position to the keto group.

In an alternative embodiment, $R_3$, $R_4$, $R_5$, $R_6$ and $R_7$ are different and two or three of them are linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl; $C_1$-$C_8$-alkoxy, preferably $C_1$-$C_6$-alkoxy and most preferably $C_1$-$C_3$-alkoxy; $C_2$-$C_8$-alkenyloxy, preferably $C_2$-$C_6$-alkenyloxy and most preferably $C_3$-$C_5$-alkenyloxy; and $C_9$-Cis-alkenylarylalkoxy, preferably $C_9$-$C_{12}$-alkenylarylalkoxy and most preferably $C_9$-$C_{10}$-alkenylarylalkoxy, and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl.

For example, $R_3$, $R_4$, $R_5$, $R_6$ and $R_7$ are different and two of them are linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl; $C_1$-$C_8$-alkoxy, preferably $C_1$-$C_6$-alkyloxy and most preferably $C_1$-$C_3$-alkyloxy; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl. Preferably, $R_3$, $R_4$, $R_5$, $R_6$ and $R_7$ are different and two of them are $C_2$-$C_8$-alkenyloxy, preferably $C_2$-$C_6$-alkenyloxy and most preferably $C_3$-$C_5$-alkenyloxy; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl, preferably the remaining ones are H.

Alternatively, $R_3$, $R_4$, $R_5$, $R_6$ and $R_7$ are different and two of them are $C_1$-$C_8$-alkoxy, preferably $C_1$-$C_6$-alkoxy and most preferably $C_1$-$C_3$-alkoxy; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl, preferably the remaining ones are H.

In one embodiment, $R_3$, $R_4$, $R_5$, $R_6$ and $R_7$ are different and three of them are $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl, preferably the remaining ones are H.

If two or three of $R_3$, $R_4$, $R_5$, $R_6$ and $R_7$ are linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl; $C_1$-$C_8$-alkoxy, preferably $C_1$-$C_6$-alkyloxy and most preferably $C_1$-$C_3$-alkyloxy; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy, it is appreciated that preferably $R_4$ and/or $R_5$ and/or $R_6$ are linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl; $C_1$-$C_8$-alkoxy, preferably $C_1$-$C_6$-alkyloxy and most preferably $C_1$-$C_3$-alkyloxy; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy.

In one embodiment, $R_3$ and $R_4$ or $R_4$ and $R_5$ form an aromatic system together with the benzene ring of general formula I, preferably a bicyclic, tricyclic or tetracyclic aromatic system, more preferably an aromatic system selected from a naphthyl, anthracenyl and phenanthrenyl system. The aromatic system is preferably a bicyclic aromatic system, most preferably naphthyl.

For example, $R_4$ and $R_5$ form an aromatic system together with the benzene ring of general formula I, preferably a bicyclic aromatic system, most preferably naphthyl; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, preferably H.

It is appreciated that one of the remaining R may be linear or branched $C_2$-$C_8$-alkenyl, preferably $C_2$-$C_6$-alkenyl and most preferably $C_2$-$C_3$-alkenyl; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy; and the remaining ones may be independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl, e.g. $C_1$- or $C_2$-alkyl, especially $C_1$-alkyl, preferably H.

In one embodiment, $R_4$ and $R_5$ form an aromatic system together with the benzene ring of general formula I, preferably a bicyclic aromatic system, most preferably naphthyl, and $R_3$ is linear or branched $C_2$-$C_8$-alkenyl, preferably $C_2$-$C_6$-alkenyl and most preferably $C_2$-$C_3$-alkenyl; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, preferably H. For example, $R_4$ and $R_5$ form an aromatic system together with the benzene ring of general formula I, preferably a bicyclic aromatic system, most preferably naphthyl, and $R_3$ is $C_9$-$C_{15}$-alkenylarylalkoxy, preferably $C_9$-$C_{12}$-alkenylarylalkoxy and most preferably $C_9$-$C_{10}$-alkenylarylalkoxy; and the remaining ones are H.

The α-functionalized ketone of the general formula I further comprises Z being selected from $OR_9$, $NHR_9$ and $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

In one embodiment, Z is $OR_9$ with $R_9$ being selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy and $C_9$-$C_{15}$-alkenylarylalkoxy, preferably $R_9$ is H or Z is $NR_{10}R_{11}$ with $R_{10}$ and $R_{11}$ being independently selected from H, linear or branched $C_1$-$C_8$-alkyl, $C_3$-$C_8$-cycloalkyl, $C_6$-$C_{14}$-aryl, or $R_{10}$ and $R_{11}$ form a $C_3$-$C_6$-alicyclic system together with the connecting N atom, optionally one or more carbon atoms are replaced with O, preferably $R_{10}$ and $R_{11}$ form a $C_5$-$C_6$-alicyclic system together with the connecting N atom and one or more carbon atoms are replaced with O.

Preferably, Z is $OR_9$ with $R_9$ being H or $NR_{10}R_{11}$ with $R_{10}$ and $R_{11}$ forming a $C_5$-$C_6$-alicyclic system, preferably a $C_6$-alicyclic system, together with the connecting N atom and one or more carbon atoms, preferably one carbon atom, is/are replaced with O.

An especially preferred α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are the same and are H, and Z is $OR_9$ with $R_9$ being H.

For example, the α-functionalized ketone of the general formula I is a ketone, wherein $R_1$ and $R_2$ are the same and are $C_1$-alkyl; $R_3$, $R_4$, $R_5$, $R_6$ and $R_7$ are the same and are H, and Z is $OR_9$ with $R_9$ being H.

Alternatively, the α-functionalized ketone of the general formula I is a ketone, wherein $R_1$ and $R_2$ form $C_3$-$C_{12}$-cycloalkyl, preferably $C_4$-$C_{10}$-cycloalkyl, more preferably $C_4$-$C_8$-cycloalkyl, even more preferably $C_4$-$C_6$-cycloalkyl, and most preferably $C_5$- or $C_6$-cycloalkyl, e.g. $C_6$-cycloalkyl, together with the connecting C atom; $R_4$, $R_5$, $R_6$ and $R_7$ are the same and are H, and Z is $OR_9$ with $R_9$ being H.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are the same and are H, and Z is $NR_{10}R_{11}$ with $R_{10}$ and $R_{11}$ forming a $C_5$-$C_6$-alicyclic system, preferably a $C_6$-alicyclic system.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are the same and are H, and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

For example, the α-functionalized ketone of the general formula I is a ketone, wherein $R_1$ and $R_2$ are the same and are $C_1$-alkyl; $R_3$, $R_4$, $R_5$, $R_6$ and $R_7$ are the same and are H, and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H and Z is $OR_9$ with $R_9$ being H.

For example, the α-functionalized ketone of the general formula I is a ketone, wherein $R_1$ and $R_2$ are the same and are $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H and Z is $OR_9$ with $R_9$ being H.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

For example, the α-functionalized ketone of the general formula I is a ketone, wherein $R_1$ and $R_2$ are the same and are $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_8$-alkyl, e.g. linear $C_1$-$C_8$-alkyl, more preferably linear or branched Cu-al-alkyl, e.g. linear Cu-al-alkyl, and most preferably linear $C_1$-$C_8$-alkyl, e.g. $C_1$- or $C_2$-alkyl, especially Cu-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_8$-alkyl, e.g. linear $C_1$-$C_8$-alkyl, more preferably linear or branched Cu-al-alkyl, e.g. linear Cu-al-alkyl, and most preferably linear $C_1$-$C_8$-alkyl, e.g. $C_1$- or $C_2$-alkyl, especially Cu-alkyl; and the remaining ones are H and Z is $OR_9$ with $R_9$ being H.

For example, the α-functionalized ketone of the general formula I is a ketone, wherein $R_1$ and $R_2$ are the same and are Cu-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially Cu-alkyl; and the remaining ones are H and Z is $OR_9$ with $R_9$ being H.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

For example, the α-functionalized ketone of the general formula I is a ketone, wherein $R_1$ and $R_2$ are the same and are $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_8$-alkyl, e.g. $C_1$- or $C_2$-alkyl, especially $C_1$-alkyl; and the remaining ones are H and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and one of them is $C_2$-$C_8$-alkenyloxy, preferably $C_2$-$C_6$-alkenyloxy and most preferably $C_3$-$C_5$-alkenyloxy, e.g. $C_3$- or $C_4$-alkenyloxy, especially $C_3$-alkenyloxy; and two of the remaining ones are H and two of the remaining ones are linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and Z is $OR_9$ with $R_9$ being H.

For example, the α-functionalized ketone of the general formula I is a ketone, wherein $R_1$ and $R_2$ are the same and are $C_1$-alkyl; $R_3$, $R_4$, $R_5$, $R_6$ and $R_7$ are different and one of them, preferably $R_5$, is $C_2$-$C_8$-alkenyloxy, preferably $C_2$-$C_6$-alkenyloxy and most preferably $C_3$-$C_5$-alkenyloxy, e.g. $C_3$- or $C_4$-alkenyloxy, especially $C_3$-alkenyloxy; and two of the remaining ones, preferably $R_3$ and $R_7$, are H and two of the remaining ones, preferably $R_4$ and $R_6$, are linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl, especially $C_1$-alkyl; and Z is $OR_9$ with $R_9$ being H.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and three of them, preferably $R_3$ and $R_4$ and $R_5$, are $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones, preferably $R_6$ and $R_7$ are H; and Z is $OR_9$ with $R_9$ being H.

For example, the α-functionalized ketone of the general formula I is a ketone, wherein $R_1$ and $R_2$ are the same and are $C_1$-alkyl; $R_3$, $R_4$, $R_5$, $R_6$ and $R_7$ are different and three of them, preferably $R_3$ and $R_4$ and $R_5$, are $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones, preferably $R_6$ and $R_7$ are H; and Z is $OR_9$ with $R_9$ being H.

Alternatively, the α-functionalized ketone of the general formula I is a ketone, wherein $R_1$ and $R_2$ are different and are selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and two of them, preferably $R_4$ and $R_5$, are $C_1$-$C_8$-alkoxy, preferably $C_1$-$C_6$-alkoxy and most preferably $C_1$-$C_3$-alkoxy, especially $C_1$-alkoxy; and the remaining ones, preferably $R_3$, $R_6$ and $R_7$, are H and Z is $OR_9$ with $R_9$ being H.

For example, the α-functionalized ketone of the general formula I is a ketone, wherein $R_1$ and $R_2$ are different and are H and $C_2$-alkyl; $R_3$, $R_4$, $R_5$, $R_6$ and $R_7$ are different and two of them, preferably $R_4$ and $R_5$, are $C_1$-$C_8$-alkoxy, preferably $C_1$-$C_6$-alkoxy and most preferably $C_1$-$C_3$-alkoxy, especially $C_1$-alkoxy; and the remaining ones, preferably $R_3$, $R_6$ and $R_7$, are H and Z is $OR_9$ with $R_9$ being H.

Alternatively, the α-functionalized ketone of the general formula I is a ketone, wherein $R_1$ and $R_2$ are different and are selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and one of them, preferably $R_5$, is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_5$- or $C_6$-alicyclic system, together with the connecting N atom, wherein one or more, preferably one, carbon atoms are replaced with O; and the remaining ones, preferably $R_3$, $R_4$, $R_6$ and $R_7$, are H and Z is $OR_9$ with $R_9$ being H.

For example, the α-functionalized ketone of the general formula I is a ketone, wherein $R_1$ and $R_2$ are different and are H and $C_2$-alkyl; $R_3$, $R_4$, $R_5$, $R_6$ and $R_7$ are different and one of them, preferably $R_5$, is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_5$- or $C_6$-alicyclic system, together with the connecting N atom, wherein one or more, preferably one, carbon atoms are replaced with O; and the remaining ones, preferably $R_3$, $R_4$, $R_6$ and $R_7$, are H and Z is $OR_9$ with $R_9$ being H.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$ and $R_5$ form an aromatic system together with the benzene ring of general formula I, preferably a bicyclic aromatic system, most preferably naphthyl; and the remaining ones are independently selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl, preferably H, and Z is $OR_9$ with $R_9$ being H.

For example, the α-functionalized ketone of the general formula I is a ketone, wherein $R_1$ and $R_2$ are the same and are $C_1$-alkyl; $R_4$ and $R_5$ form an aromatic system together with the benzene ring of general formula I, preferably a bicyclic aromatic system, most preferably naphthyl; and the remaining ones are H and Z is $OR_9$ with $R_9$ being H.

Alternatively, the α-functionalized ketone of the general formula I is a ketone, wherein $R_1$ and $R_2$ are the same and are selected from linear or branched $C_1$-$C_5$-alkyl, e.g. linear $C_1$-$C_5$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$ and $R_5$ form an aromatic system together with the benzene ring of general formula I, preferably a bicyclic aromatic system, most preferably naphthyl; and one of the remaining R, preferably $R_3$, is linear or branched $C_2$-$C_5$-alkenyl, preferably $C_2$-$C_6$-alkenyl and most preferably $C_2$-$C_3$-alkenyl; $C_2$-$C_5$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy and the remaining ones are H, and Z is $OR_9$ with $R_9$ being H.

For example, the α-functionalized ketone of the general formula I is a ketone, wherein $R_1$ and $R_2$ are the same and are $C_1$-alkyl; $R_4$ and $R_5$ form an aromatic system together with the benzene ring of general formula I, preferably a bicyclic aromatic system, most preferably naphthyl; and one of the remaining R, preferably $R_3$, is $C_9$-$C_{15}$-alkenylarylalkoxy, preferably $C_9$-$C_{12}$-alkenylarylalkoxy and most preferably $C_9$-$C_{10}$-alkenylarylalkoxy and the remaining ones are H, and Z is $OR_9$ with $R_9$ being H.

It is appreciated that the α-functionalized ketone of the general formula I is prepared by a specific process, namely a one-pot process, avoiding elaborate purification steps for obtaining the desired α-functionalized ketones. The yield and purity of the desired α-functionalized ketones are thus significantly increased. Furthermore, the process allows the preparation of α-functionalized ketones that have not been accessible by the processes of the prior art up to now and thus also results in new α-functionalized ketones that can be used as photoinitiators.

The process is characterized in that a ketone of the general formula II

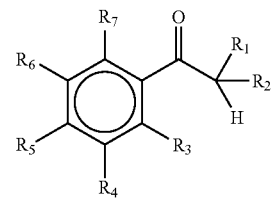

wherein $R_1$, $R_2$, $R_3$, $R_4$, $R_5$, $R_6$ and $R_7$ are as defined above, is contacted under phase-transfer conditions with an at least partially halogenated $C_2$-$C_8$-alkane and/or $C_2$-$C_8$-alkene, and a base selected from the group comprising alkali metal hydroxide, earth alkali metal hydroxide, alkali metal $C_1$-$C_8$-alkoxide, earth alkali metal $C_1$-$C_8$-alkoxide and mixtures thereof, or a base selected from the group comprising alkali metal hydroxide, earth alkali metal hydroxide, alkali metal $C_1$-$C_8$-alkoxide, earth alkali metal $C_1$-$C_8$-alkoxide and mixtures thereof together with the protonated form of Z as defined above.

With regard to the definition of the α-functionalized ketone, the $R_1$, $R_2$, $R_3$, $R_4$, $R_5$, $R_6$ and $R_7$ and preferred embodiments thereof, reference is made to the statements provided above when discussing the technical details of the α-functionalized ketone of the general formula I obtained by process of the present invention.

In one embodiment, the ketone of the general formula II is contacted under phase-transfer conditions with the at least partially halogenated $C_2$-$C_8$-alkane and/or $C_2$-$C_8$-alkene, and the base together with the protonated form of Z.

With regard to the definition of Z and preferred embodiments thereof, reference is made to the statements provided above when discussing the technical details of the α-functionalized ketone of the general formula I obtained by the process of the present invention. Accordingly, it is to be noted that the skilled person will readily understand what is meant by the wording "protonated form of Z".

However, the process is preferably carried out by contacting the ketone of the general formula II under phase-transfer conditions with the at least partially halogenated $C_2$-$C_8$-alkane and/or $C_2$-$C_8$-alkene, and the base together with the protonated form of Z, if Z in general formula I is $NHR_9$ or $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-Cis-arylalkoxy, $C_9$-Cis-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

Accordingly, the protonated form of Z is preferably $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

It is preferred that the at least partially halogenated $C_2$-$C_8$-alkane and/or $C_2$-$C_8$-alkene is an at least partially halogenated $C_2$-$C_6$-alkane and/or $C_2$-$C_6$-alkene, more preferably an at least partially halogenated $C_2$-$C_4$-alkane and/or $C_2$-$C_4$-alkene. For example, the at least partially halogenated $C_2$-$C_8$-alkane and/or $C_2$-$C_8$-alkene is an at least partially halogenated $C_2$- or $C_3$-alkane and/or $C_2$- or $C_3$-alkene, e.g. an at least partially halogenated $C_2$-alkane and/or $C_2$-alkene.

The at least partially halogenated $C_2$-$C_8$-alkane and/or $C_2$-$C_8$-alkene may be at least partially chlorinated and/or brominated. For example, the at least partially halogenated $C_2$-$C_8$-alkane and/or $C_2$-$C_8$-alkene is at least partially chlorinated or brominated. Alternatively, the at least partially halogenated $C_2$-$C_8$-alkane and/or $C_2$-$C_8$-alkene is at least partially chlorinated and brominated, and thus is a mixed halogenated $C_2$-$C_8$-alkane and/or $C_2$-$C_8$-alkene.

Preferably, the at least partially halogenated $C_2$-$C_8$-alkane and/or $C_2$-$C_8$-alkene is at least partially chlorinated.

In one embodiment, the at least partially halogenated $C_2$-$C_8$-alkane and/or $C_2$-$C_8$-alkene is fully halogenated. Preferably, the at least partially halogenated $C_2$-$C_8$-alkane and/or $C_2$-$C_8$-alkene is a fully halogenated $C_2$-$C_6$-alkane and/or $C_2$-$C_6$-alkene, more preferably a fully halogenated $C_2$-$C_4$-alkane and/or $C_2$-$C_4$-alkene. For example, the at least partially halogenated $C_2$-$C_8$-alkane and/or $C_2$-$C_8$-alkene is a fully halogenated $C_2$- or $C_3$-alkane and/or $C_2$- or $C_3$-alkene.

For example, the at least partially halogenated $C_2$-$C_8$-alkane and/or $C_2$-$C_8$-alkene may be fully chlorinated and/or brominated. For example, the at least partially halogenated $C_2$-$C_8$-alkane and/or $C_2$-$C_8$-alkene is fully chlorinated or brominated. Alternatively, the at least partially halogenated $C_2$-$C_8$-alkane and/or $C_2$-$C_8$-alkene is fully chlorinated and brominated, and thus is a mixed halogenated $C_2$-$C_8$-alkane and/or $C_2$-$C_8$-alkene.

Preferably, the at least partially halogenated $C_2$-$C_8$-alkane and/or $C_2$-$C_8$-alkene is fully chlorinated.

In one embodiment, the at least partially halogenated $C_2$-$C_8$-alkane and/or $C_2$-$C_8$-alkene is selected from hexachloroethane, tetrachoroethylene, pentachloropropane, hexabromoethane, tetrabromoethylene, pentabromopropane and mixtures thereof. Preferably, the at least partially halogenated $C_2$-$C_8$-alkane and/or $C_2$-$C_8$-alkene is hexachloroethane, tetrachoroethylene and mixtures thereof. For example, the at least partially halogenated $C_2$-$C_8$-alkane and/or $C_2$-$C_8$-alkene is hexachloroethane or tetrachoroethylene.

In one embodiment, the at least partially halogenated $C_2$-$C_8$-alkane and/or $C_2$-$C_8$-alkene is hexachloroethane and tetrachoroethylene.

Another essential component of the process is the addition of a base. It is a requirement of the present invention that the base is selected from the group comprising alkali metal hydroxide, earth alkali metal hydroxide, alkali metal $C_1$-$C_8$-alkoxide, earth alkali metal $C_1$-$C_8$-alkoxide and mixtures thereof, or a base selected from the group comprising alkali metal hydroxide, earth alkali metal hydroxide, alkali metal $C_1$-$C_8$-alkoxide, earth alkali metal $C_1$-$C_8$-alkoxide and mixtures thereof together with the protonated form of Z as defined above.

In one embodiment, the base is selected from the group comprising sodium hydroxide; lithium hydroxide; potassium hydroxide; sodium $C_1$-$C_6$-alkoxide, preferably sodium $C_1$-$C_4$-alkoxide and most preferably sodium $C_1$-$C_2$-alkoxide; lithium $C_1$-$C_6$-alkoxide, preferably lithium $C_1$-$C_4$-alkoxide and most preferably lithium $C_1$-$C_2$-alkoxide; potassium $C_1$-$C_6$-alkoxide, preferably potassium $C_1$-$C_4$-alkoxide and most preferably potassium $C_1$-$C_2$-alkoxide; and mixtures thereof. Preferably, the base is selected from the group comprising sodium hydroxide and sodium $C_1$-$C_6$-alkoxide, preferably sodium $C_1$-$C_4$-alkoxide and most preferably sodium $C_1$-$C_2$-alkoxide. Most preferably, the base is sodium hydroxide. This embodiment is especially preferred if Z in general formula I is $OR_9$, with $R_9$, being H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-Cis-alkenylarylalkyl.

Alternatively, the base is selected from sodium $C_1$-$C_6$-alkoxide, preferably sodium $C_1$-$C_4$-alkoxide and most preferably sodium $C_1$-$C_2$-alkoxide; lithium $C_1$-$C_6$-alkoxide, preferably lithium $C_1$-$C_4$-alkoxide and most preferably lithium $C_1$-$C_2$-alkoxide; potassium $C_1$-$C_6$-alkoxide, preferably potassium $C_1$-$C_4$-alkoxide and most preferably potassium $C_1$-$C_2$-alkoxide, and mixtures thereof, together with the protonated form of Z as defined above. Preferably, the base is selected from the group comprising sodium hydroxide and sodium $C_1$-$C_6$-alkoxide, preferably sodium $C_1$-$C_4$-alkoxide and most preferably sodium $C_1$-$C_2$-alkoxide, and mixtures thereof. In one embodiment, the base is sodium hydroxide and/or sodium $C_1$-alkoxide. For example, the base is sodium hydroxide and sodium $C_1$-alkoxide, i.e. a mixture of sodium hydroxide and sodium $C_1$-alkoxide. Alternatively, the base is sodium hydroxide or sodium $C_1$-alkoxide, preferably sodium hydroxide. The combination of a base with the protonated form of Z is especially preferred if Z in general formula I is $NHR_9$ or $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

The base can be added as such to the process. Alternatively, the base is in form of an aqueous solution or the base is provided in an organic solvent, preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3-dioxane or 1,4-dioxane, 1,2-dimethoxyethane, diethyleneglycol dimethyl ether, triethyleneglycol dimethyl ether and mixtures thereof. Preferably, the base is provided in an organic solvent, preferably the organic solvent is tetrachloroethylene.

The process of the present invention can be carried out over a wide temperature range. However, it is preferred that the process is carried out at elevated temperature. For example, the process is carried out at a temperature of at least 30° C., preferably in the range from 30 to 120° C., more preferably in the range from 40 to 100° C., and most preferably in the range from 40 to 90° C.

It is further appreciated that the process can be carried out in an organic solvent. Preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3- dioxane or 1,4-dioxane, 1,2-dimethoxyethane, diethyleneglycol dimethyl ether, triethyleneglycol dimethyl ether and mixtures thereof.

If the base is provided in an organic solvent, the organic solvent is preferably the same as used in the process.

It is a further requirement of the present invention that the process is carried out under phase-transfer conditions. Such phase-transfer conditions are well known in the art such that the skilled person will easily apply reaction conditions that are suitable for the reaction mentioned. The skilled person can also apply variants of such reactions which are known per se and are not mentioned herein in detail.

In particular, the contacting of the compound of formula II is carried out in the presence of a phase-transfer catalyst with the at least partially halogenated $C_2$-$C_8$-alkane and/or $C_2$-$C_8$-alkene, and a base selected from the group comprising alkali metal hydroxide, earth alkali metal hydroxide, alkali metal $C_1$-$C_8$-alkoxide, earth alkali metal $C_1$-$C_8$-alkoxide and mixtures thereof, or a base selected from the group comprising alkali metal hydroxide, earth alkali metal hydroxide, alkali metal $C_1$-$C_8$-alkoxide, earth alkali metal $C_1$-$C_8$-alkoxide and mixtures thereof together with the protonated form of Z as defined above.

The phase-transfer catalyst can be selected from any phase-transfer catalyst known in the art. However, the phase-transfer catalyst is preferably selected from a quaternary ammonium salt, tetraalkylphosphonium chloride, tetraalkylphosphonium bromide and mixtures thereof. More preferably, the phase-transfer catalyst is a tetraalkylammonium salt or a trialkylarylammonium salt, and most preferably the phase-transfer catalyst is selected from the group comprising benzyltrimethylammonium hydroxide, benzyltriethylammonium chloride, tetrabutylammonium chloride, tetrabutylammonium bromide, tetrabutylammonium hydrogensulfate, tetrabutylammonium hydroxide, methyltrioctylammonium chloride, cetyl pyridinium and mixtures thereof.

Such phase-transfer catalysts are well known in the art such that the skilled person will easily apply catalysts that are suitable for the reaction mentioned. The skilled person can also apply variants of such catalysts which are known per se and are not mentioned herein in detail.

The amount of phase-transfer catalysts can be chosen as desired within wide limits, preferably being 0.1 to 100 wt.-%, based on the weight of the ketone of the general formula II.

One advantage of the present process is that the process can be carried out in a one-pot process, and thus avoids elaborate purification steps for obtaining the desired α-functionalized ketones. The yield and purity of the desired α-functionalized ketones are thus significantly increased.

The term "one-pot process" in the meaning of the present invention refers to a process that can be carried out without the isolation and purification of intermediate products.

It is thus appreciated that the α-functionalized ketone is obtained in a one-pot reaction.

It has been found that the sequence of addition of the reagents is important for the success of the reaction. The best yields are obtained when the ketone of the general formula II, the phase-transfer catalyst, the base selected from the group comprising alkali metal hydroxide, earth alkali metal hydroxide, alkali metal $C_1$-$C_8$-alkoxide, earth alkali metal $C_1$-$C_8$-alkoxide and mixtures thereof, or the base selected from the group comprising alkali metal hydroxide, earth alkali metal hydroxide, alkali metal $C_1$-$C_8$-alkoxide, earth alkali metal $C_1$-$C_8$-alkoxide and mixtures thereof together with the protonated form of Z as defined above and, if present, the organic solvent are contacted first and the at least partially halogenated $C_2$-$C_8$-alkane and/or $C_2$-$C_8$-alkene is metered in.

The reaction and contacting are carried out by mixing the components, i.e. the ketone of the general formula II, the phase-transfer catalyst, the at least partially halogenated $C_2$-$C_8$-alkane and/or $C_2$-$C_8$-alkene, and the base selected from the group comprising alkali metal hydroxide, earth alkali metal hydroxide, alkali metal $C_1$-$C_8$-alkoxide, earth alkali metal $C_1$-$C_8$-alkoxide and mixtures thereof, or the base selected from the group comprising alkali metal hydroxide, earth alkali metal hydroxide, alkali metal $C_1$-$C_8$-alkoxide, earth alkali metal $C_1$-$C_8$-alkoxide and mixtures thereof together with the protonated form of Z as defined above. The skilled person will adapt the mixing conditions (such as the configuration of mixing tools and mixing speed) according to his process equipment.

The process of the present invention may comprise further steps for isolating and/or purifying the obtained α-functionalized ketones of general formula I.

For example, the process may further comprise a step of
i) separating the obtained organic and aqueous phases, and/or
ii) extracting the obtained aqueous phase with the organic solvent used in the process and combining the obtained organic phases, and/or
iii) acidifying the obtained organic phase to a pH of 3 to 6.5.

In one embodiment, the process further comprises the steps of
i) separating the obtained organic and aqueous phases, and
ii) extracting the obtained aqueous phase with the organic solvent used in the process and combining the obtained organic phases, and
iii) acidifying the obtained organic phase to a pH of 3 to 6.5.

Additionally, the process may further comprise a step of drying the obtained α-functionalized ketones of general formula I.

The ketone of the general formula II used can be easily α-functionalized in high yields and purity. The residue from work-up, which consists mainly of organic solvent and (unchanged) phase-transfer catalyst, can be reused e.g. in the process as solvent and (re-halogenated) phase-transfer catalyst.

According to another aspect, an α-functionalized ketone obtained by the process as defined herein, is provided.

Thus, the α-functionalized ketone of the present invention is obtained by a process comprising the contacting of a ketone of the general formula II

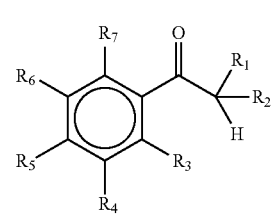

wherein $R_1$, $R_2$, $R_3$, $R_4$, $R_5$, $R_6$ and $R_7$ are as defined above, under phase-transfer conditions with an at least partially halogenated $C_2$-$C_8$-alkane and/or $C_2$-$C_8$-alkene, and a base selected from the group comprising alkali metal hydroxide, earth alkali metal hydroxide, alkali metal $C_1$-$C_8$-alkoxide, earth alkali metal $C_1$-$C_8$-alkoxide and mixtures thereof, or a base selected from the group comprising alkali metal hydroxide, earth alkali metal hydroxide, alkali metal $C_1$-$C_8$-alkoxide, earth alkali metal $C_1$-$C_8$-alkoxide and mixtures thereof together with the protonated form of Z as defined above.

With regard to the definition of the α-functionalized ketone, the ketone of the general formula II, the $R_1$, $R_2$, $R_3$, $R_4$, $R_5$, $R_6$ and $R_7$ and preferred embodiments thereof, reference is made to the statements provided above when discussing the technical details of the process and the α-functionalized ketone of the general formula I obtained by the process of the present invention.

The inventors surprisingly found that the process allows the preparation of α-functionalized ketones that have not been accessible by the processes of the prior art up to now and thus also results in new α-functionalized ketones that can be used as photo initiator.

In another aspect, the present invention thus refers to an α-functionalized ketone as defined herein, with the proviso that at least one of $R_3$, $R_4$, $R_5$, $R_6$ and $R_7$ is linear or branched $C_2$-$C_8$-alkenyl, preferably $C_2$-$C_6$-alkenyl and most preferably $C_2$-$C_3$-alkenyl, $C_2$-$C_8$-alkenyloxy, preferably $C_2$-$C_6$-alkenyloxy and most preferably $C_3$-$C_8$-alkenyloxy, and $C_9$-$C_{15}$-alkenylarylalkoxy, preferably $C_9$-$C_{12}$-alkenylarylalkoxy and most preferably $C_9$-$C_{10}$-alkenylarylalkoxy. The α-functionalized ketone is preferably obtained by the process of the present invention.

The new α-functionalized ketone is thus preferably an α-functionalized ketone of the general formula I,

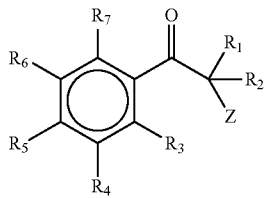

I wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom; $R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy or $R_8$ form a $C_3$-$C_9$-alicyclic system together with the connecting N atom, optionally one or more carbon atoms are replaced with O, or two adjacent R form an aromatic system together with the benzene ring of formula I; Z is selected from $OR_9$, $NHR_9$ and $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O; with the proviso that at least one of $R_3$, $R_4$, $R_5$, $R_6$ and $R_7$ is linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl, $C_2$-$C_8$-alkenyloxy, preferably $C_2$-$C_6$-alkenyloxy and most preferably $C_3$-$C_5$-alkenyloxy, and $C_9$-$C_{15}$-alkenylarylalkoxy, preferably $C_9$-$C_{12}$-alkenylarylalkoxy and most preferably $C_9$-$C_{10}$-alkenylarylalkoxy.

With regard to the definition of the α-functionalized ketone, $R_1$, $R_2$, $R_3$, $R_4$, $R_5$, $R_6$, $R_7$ and Z and preferred embodiments thereof, reference is made to the statements provided above when discussing the technical details of the process and the α-functionalized ketone of the general formula I obtained by the process of the present invention.

A further aspect of the present invention thus refers to the use of the new α-functionalized ketone as photoinitiator.

More precisely, the present invention also relates to the use of an α-functionalized ketone of the general formula I as photoinitiator,

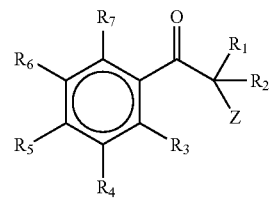

I wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom; $R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy or $R_8$ form a $C_3$-$C_9$-alicyclic system together with the connecting N atom, optionally one or more carbon atoms are replaced with O, or two adjacent R form an aromatic system together with the benzene ring of formula I; Z is selected from $OR_9$, $NHR_9$ and $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O; with the proviso that at least one of $R_3$, $R_4$, $R_5$, $R_6$ and $R_7$ is linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl, $C_2$-$C_8$-alkenyloxy, preferably $C_2$-$C_6$-alkenyloxy and most preferably $C_3$-$C_5$-alkenyloxy, and $C_9$-$C_{15}$-alkenylarylalkoxy, preferably $C_9$-$C_{12}$-alkenylarylalkoxy and most preferably $C_9$-$C_{10}$-alkenylarylalkoxy.

With regard to the definition of the α-functionalized ketone, $R_1$, $R_2$, $R_3$, $R_4$, $R_5$, $R_6$, $R_7$ and Z and preferred embodiments thereof, reference is made to the statements provided above when discussing the technical details of the process and the α-functionalized ketone of the general formula I obtained by the process of the present invention.

A further aspect of the present invention refers to a photopolymerizable composition comprising the α-functionalized ketone as defined herein and at least one photopolymerizable unsaturated compound.

It is appreciated that any photopolymerizable unsaturated compound that is typically used in the articles to be prepared and is well known can be used as the at least one photopolymerizable unsaturated compound. For example, the at least one photopolymerizable unsaturated compound can be a compound as described in WO 2004/099262 A1 which is thus incorporated herewith by reference.

The photopolymerizable composition may also contain optional additives and/or optional further photoinitiators and/or coinitiator. The optional additives and/or photoinitiators and/or coinitiator are not limited any include any additive and/or photoinitiators and/or coinitiator typically used in the articles to be prepared and are well known in the art. For example, the additives and/or photoinitiators and/or coinitiator can be one or more compounds described as additives (C) and/or photoinitiators and/or coinitiator (D) in WO 2004/099262 A1 which is thus incorporated herewith by reference.

A further aspect of the present invention thus refers to the use of the photopolymerizable composition comprising the α-functionalized ketone and at least one photopolymerizable unsaturated compound, as defined herein, as photoinitiator.

It is preferred that the α-functionalized ketone of the general formula I or the photopolymerizable composition comprising the α-functionalized ketone and at least one photopolymerizable unsaturated compound as defined herein is used as photoinitiator in a method of preparing an article.

Thus, the α-functionalized ketone of the general formula I or the photopolymerizable composition comprising the α-functionalized ketone and at least one photopolymerizable unsaturated compound as defined herein is preferably used as photoinitiator in an article, preferably a packaging article, more preferably a food or beverage packaging article, an article of flooring or an article of furniture.

With regard to the definition of the α-functionalized ketone, the photopolymerizable composition and preferred embodiments thereof, reference is made to the statements provided above when discussing the technical details of the process and the α-functionalized ketone of the general formula I obtained by the process of the present invention.

In view of the advantages obtained, the present invention refers in another aspect to a method of preparing an article. The method comprising the steps of
a) preparing a coating and/or ink composition comprising the α-functionalized ketone as defined herein or the photopolymerizable composition comprising an α-functionalized ketone as defined herein,
b) applying the coating and/or ink composition at least partially on at least one surface of an article, and
c) curing the coating and/or ink composition by means of ultra-violet radiation.

With regard to the definition of the α-functionalized ketone, the photopolymerizable composition and preferred embodiments thereof, reference is made to the statements provided above when discussing the technical details of the process and the α-functionalized ketone of the general formula I obtained by the process of the present invention.

It is appreciated that coating and/or ink compositions are well known to the skilled person and do not need to be described in more detail in the present application. Thus, any coating and/or ink composition that is typically used for the articles to be prepared and is well known can be used. The person skilled in the art will adapt the coating and/or ink composition according to the article to be prepared and/or his process equipment.

Furthermore, any suitable application means known in the art may be used for carrying out application step b). However, application step b) is preferably carried out by brushing, dripping, printing, spraying, dipping and the like. Most preferably, application step b) takes place by spraying.

For the purposes of the present invention, any suitable curing means using ultra-violet radiation known in the art may be used for carrying out curing step c). Such curing steps are well known in the art and the skilled person will adapt the curing conditions according to his process equipment and the article to be prepared.

In view of the above, the present invention refers in another aspect to an article obtained by a method of preparing an article, as defined herein.

It is preferred that the article is a packaging article, an article of flooring or an article of furniture. If the article is a packaging article, the article is preferably a food or beverage packaging article. If the article is an article of flooring, the article is preferably a tile, most preferably a ceramic, vinyl or composite tile, or a floorboard, most preferably a wooden or composite floorboard.

The scope and interest of the invention will be better understood based on the following examples which are intended to illustrate certain embodiments of the invention and are non-limitative.

EXAMPLES

Example 1: Preparation of 2-hydroxy-2-methyl-1-phenyl-1-propanone

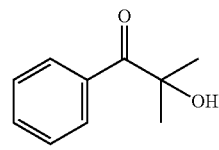

A 500 mL double-walled-jacket, multi-necked flask, fitted with a mechanical stirrer, reflux condenser, connected to a thermostat, thermometer and a dropping funnel, is charged with 59.3 g (400 mmol) isobutyrophenone, 2.58 g (8 mmol) tetrabutylammonium bromide and 373.3 g (2.80 mol) 30% aqueous sodium hydroxide solution. This is heated with stirring to 82-85° C., and within 90 minutes a solution of 94.7 g (408 mmol) hexachloroethane in 199 g tetrachloroethylene is added. The reaction mixture is stirred for another 3 hours at 84° C. The temperature is then lowered to 60° C. and left unstirred for phase separation. The lower organic phase is split off; the aqueous phase is extracted with 50 g tetrachloroethylene, the organic phases are combined and 100 g water added. pH is then adjusted to 6.0 using 5% acetic acid. The organic phase is split off and distilled in vacuo.

Yield: 56.8 g (86.5%) 2-Hydroxy-2-methyl-1-phenyl-1-propanone as a pale yellow oil; b.p. 96° C., 1 mbar, 99% purity (GC). NMR data are identical with the data of an authentic reference sample.

Tetrachloroethylene (b.p. 55° C., 200 mbar) is nearly quantitatively recovered (94%, 99.6% purity).

Example 2: Preparation of (1-hydroxycyclohexyl) phenyl Ketone

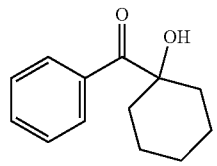 [SMILES: O=C(c1ccccc1)C1(O)CCCCC1]

A 500 mL double-walled-jacket multi-necked flask, fitted with a mechanical stirrer, reflux condenser, thermometer and a dropping funnel connected to a thermostat, is charged with 75.3 g (400 mmol) cyclohexyl phenyl ketone, 2.58 g (8 mmol) tetrabutylammonium bromide and 373.3 g (2.80 mol) 30% aqueous sodium hydroxide solution. This is heated with stirring to 82-85° C. and within 90 minutes a solution of 96.6 g (408 mmol) hexachloroethane in 199 g tetrachloroethylene is added. The reaction mixture is stirred for another 3 hours at 84° C. The temperature is then lowered to 60° C. and left unstirred for phase separation. The lower organic phase is split off; the aqueous phase is extracted with 50 g tetrachloroethylene, the organic phases are combined and 100 g water added. pH is then adjusted to 6.0 using 5% acetic acid. The organic phase is split off and the product is vacuum distilled.

Yield: 66.3 g (81.2%) (1-hydroxycyclohexyl) phenyl ketone (Irgacure 184) as a pale yellow oil;

b.p. 143° C., 0.7 mbar, 95% purity (GC). NMR data are identical with the data of an authentic reference sample.

Tetrachloroethylene (b.p. 55° C., 200 mbar) is nearly quantitatively recovered (97%, 99.5% purity).

Example 3: Preparation of 2-hydroxy-2-methyl-1-(4-vinylphenyl)propan-1-one

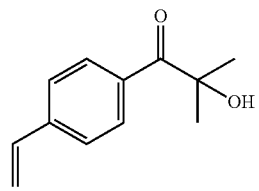

To a multi-necked, double-walled-jacket 500 mL flask, fitted with a thermometer, reflux condenser and a mechanical stirrer was charged 4-vinylisobutyrophenone (1.20 g, 6.89 mmol), tetrabutylammonium bromide (44 mg, 0.14 mmol), sodium hydroxide solution 30% (6.5 g, 48.8 mmol), tetrachloroethylene (6 g) and ProStab (1% solution in toluene, 0.02 g). The mixture was heated to 50° C. with stirring and a solution of hexachloroethane (2.19 g, 9.25 mmol) in tetrachloroethylene (5 g) is added dropwise within 30 minutes time. Stirring is continued overnight at 50° C., the reaction mixture cooled to ambient temperature and extracted with tetrachloroethylene (3×10 mL). The organic phase is acidified to pH 4 with 5% acetic acid, washed with water (3×10 mL) and dried with sodium sulfate. The solvent is evaporated to give the product [1.12 g, 5.89 mmol, 86%] as a pale yellow oil.

$^1$H-NMR (400.1 MHz, CDCl$_3$): δ=1.61 (s, 6H), 4.16 (br. s, 1H), 5.40 (dd, 1H), 5.87 (dd, 1H), 6.74 (dd, 1H), 7.44-7.48 (m, 2H), 7.98-8.02 ppm (m, 2H).

Example 4: Preparation of 1-(4-allyloxy-3,5-dimethyl-phenyl)-2-hydroxy-2-methyl-propan-1-one

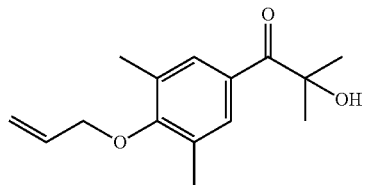 [SMILES: C=CCOc1c(C)cc(C(=O)C(C)(C)O)cc1C]

To a reaction flask containing 100 ml of benzene and the solution of NaOH (40 g, 1 mol) in 40 ml of water is added tetrabutylammonium bromide (2 g), 1-(4-allyloxy-3,5-dimethyl-phenyl)-2-methyl-propan-1-one (19.15 g, 0.082 mol, prepared as described below) and hexachloroethane (39 g, 0.165 mol). The heterogeneous mixture is vigorously stirred under nitrogen during 90 minutes at 60° C. The mixture is then cooled to room temperature and diluted with 300 ml of water and 250 ml of t-butyl-methyl ether. The organic phase is separated and the aqueous phase is extracted with 200 ml of t-butyl-methyl ether. The combined organic phases are dried over magnesium sulfate and evaporated. The semisolid product (34 g) is chromatographed on silica gel with hexane-ethyl acetate (4:1) to afford 18.69 g of the title product as a light yellow oil.

$^1$H-NMR (CDCl$_3$, 400 MHz, δ ppm): 7.73 (s, 2ArH), 6.15-6.07 (m, 1H), 5.48-5.47 (dd, 1H), 5.44-5.42 (dd, 1H), 4.38-4.36 (d, 2H, CH$_2$), 4.22 (s, 1H, OH), 2.34 (s, 2×CH$_3$), 1.64 (s, 2×CH$_3$)

Example 5 (Comparative Example to Example 4): Preparation of 1-(4-allyloxy-3,5-dimethyl-phenyl)-2-hydroxy-2-methyl-propan-1-one Using Tetrachloromethane Running the reaction described in example 4 under same conditions, but replacing hexachloroethane with tetrachloromethane, leads to the formation of a considerable amount (~10%) of the side-product 1-[4-[(2,2-dichlorocyclopropyl)-methoxy]-3,5-dimethyl-phenyl]-2-hydroxy-2-methyl-propan-1-one.

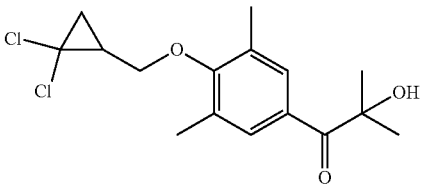 [SMILES: Cc1cc(C(=O)C(C)(C)O)cc(C)c1OCC1CC1(Cl)Cl]

Analytical data for 1-[4-[(2,2-dichlorocyclopropyl)-methoxy]-3,5-dimethyl-phenyl]-2-hydroxy-2-methyl-propan-1-one:
Colorless Oil MS for C$_{16}$H$_{20}$Cl$_2$O$_3$ (331.23); found M=331.

$^1$H-NMR (CDCl$_3$, 400 MHz, δ ppm): 7.72 (s, 2 ArH), 4.20 (s, 1H, OH), 4.06-3.91 (m, 2H, CH$_2$—O), 2.36 (s, 2×CH$_3$), 2.19-2.11 (m, 1H), 1.77-1.72 (m, 1H), 1.61 (s, 2×CH$_3$), 1.35-1.25 (s, 1H).

Example 6: Preparation of 2-hydroxy-2-methyl-1-(1-naphthyl)propan-1-one

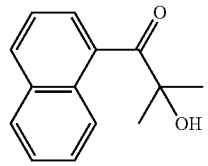 [SMILES: CC(C)(O)C(=O)c1cccc2ccccc12]

Using the same equipment as in examples 1-5, to a mixture of 1-isobutyronaphthone (1.40 g, 7.06 mmol), tetrabutylammonium bromide (46 mg, 0.14 mmol), sodium hydroxide solution 30% (6.6 g, 49.5 mmol) and tetrachloroethylene (5 g) is added hexachloroethane (1.84 g, 7.77 mmol) dissolved in tetrachloroethylene (4 g). This mixture is stirred at 50° C. for 4.5 h. After cooling to room temperature, acetic acid 5% is added to adjust pH to 4 and the organic phase is washed with water (3×10 mL). The organic phase is dried over sodium sulfate and the evaporated to dryness. The crude product is purified by column chromatography [c-C$_6$H$_{12}$/AcOEt, 4:1 v:v] and the title compound is isolated as a pale yellow oil [0.95 g, 4.43 mmol, 63%].

$^1$H-NMR (400.1 MHz, CDCl$_3$): δ=1.52 (s, 6H), 3.87 (s, 1H), 7.43 (dd, 1H), 7.47-7.53 (m, 2H), 7.56 (dd, 1H), 7.73-7.79 (m, 1H), 7.82-7.87 (m, 1H), 7.88-7.91 ppm (m, 1H)

Example 7: Preparation of 2-hydroxy-2-methyl-1-(2-naphthyl)propan-1-one

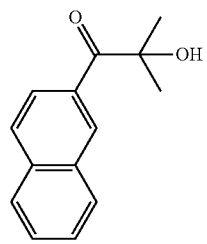 [SMILES: CC(C)(O)C(=O)c1ccc2ccccc2c1]

A 25 mL three-necked flask is charged 2-isobutyronaphthone (0.50 g, 2.52 mmol), tetrabutylammoniumbromide (16 mg, 0.05 mmol), sodium hydroxide solution (30%, 2.35 g, 17.65 mmol) and tetrachloroethylene (10 g). To this is added hexachloroethane (0.66 g, 2.77 mmol), dissolved in tetrachlorethylene (2.5 g) and the reaction mixture is stirred at 50° C. overnight. After cooling to room temperature, pH is adjusted to 4 with 5% acetic acid and the organic phase washed with water (3×10 mL). The organic phase is dried over sodium sulfate and the solution evaporated to dryness. The crude product is purified by column chromatography on silicagel [c-C$_6$H$_{12}$/AcOEt, 9:1 v:v], providing the title compound as a yellowish oil.

$^1$H-NMR (400.1 MHz, CDCl$_3$): δ=1.71 (s, 6H), 4.16 (s, 1H), 7.53-7.63 (m, 2H), 7.85-7.89 (m, 2H), 7.95 (dd, 1H), 8.05 (dd, 1H), 8.60 (d, 1H)

Example 8: Preparation of 2-hydroxy-2-methyl-1-[1-[(4-vinylphenyl)methoxy]-2-naphthyl]propan-1-one

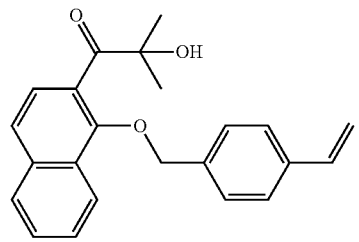 [SMILES: C=Cc1ccc(COc2c(C(=O)C(C)(C)O)ccc3ccccc23)cc1]

To a mixture of 2-methyl-1-[1-[(4-vinylphenyl)methoxy]-2-naphthyl]propan-1-one (0.40 g, 1.21 mmol), tetrabutylammonium bromide (8 mg, 0.02 mmol), sodium hydroxide solution (30%, 1.13 g, 8.47 mmol) and tetrachloroethylene (3.5 g) is added a solution of hexachloroethane (0.32 g, 1.33 mmol) in tetrachloroethylene (1 g) at 50° C. Stirring is continued for 4 h at 50° C. After cooling to room temperature, the organic phase is split off and the aqueous phase is extracted with tetrachloroethylene (3×10 mL). After pH of the organic phase is adjusted to 4 (5% acetic acid), the organic phase is washed with water (3×10 mL), dried over sodium sulfate and evaporated to dryness. The crude product is subjected to column chromatography [c-C$_6$H$_{12}$/AcOEt, 19:1 v:v] to give the title compound [0.42 g, 1.96 mmol, 78%] as a slightly yellow oil.

$^1$H-NMR (400.1 MHz, CDCl$_3$): δ=1.45 (s, 6H), 3.96 (s, 1H), 5.04 (s, 2H), 5.27 (dd, 1H), 5.77 (dd, 1H), 6.73 (dd, 1H), 7.31 (d, 1H), 7.40-7.47 (m, 4H), 7.51-7.57 (m, 2H), 7.67 (d, 1H), 7.84-7.90 (m, 1H), 8.11-8.16 ppm (m, 1H);
$^{13}$C-NMR (100.6 MHz, CDCl$_3$): δ=27.2, 78.3, 114.4, 122.5, 124.0, 124.7, 126.6, 127.0, 127.5, 127.7, 128.3, 128.9, 130.8, 135.7, 135.9, 136.4, 137.9, 151.7, 212.0 ppm Example 9: Preparation of 2-hydroxy-2-methyl-1-[2,3,4-tris[(4-vinylphenyl)methoxy]-phenyl]propan-1-one

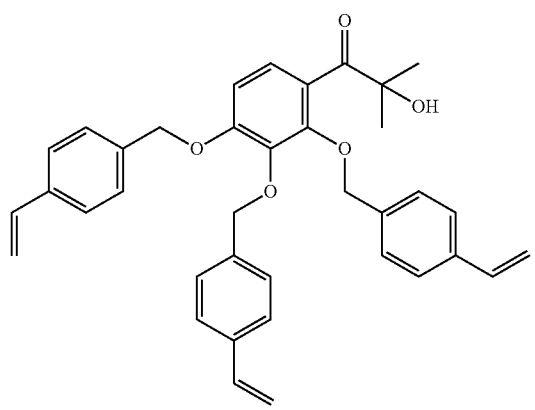 [SMILES: C=Cc1ccc(COc2ccc(C(=O)C(C)(C)O)c(OCc3ccc(C=C)cc3)c2OCc2ccc(C=C)cc2)cc1]

To a 25 mL three-necked flask is charged 2-methyl-1-[2,3,4-tris[(4-vinylphenyl)methoxy]phenyl]propan-1-one (250 mg, 0.46 mmol), tetrabutylammonium bromide (3 mg, 0.01 mmol), sodium hydroxide solution (30%, 0.43 g, 3.22 mmol) and tetrachloroethylene (2.5 g). To this is added a solution of hexachloroethane (120 mg, 0.50 mmol) in tetrachlorethylene (0.8 g). The reaction mixture is stirred at 50° C. overnight. The reaction mixture is allowed to come to room temperature and extracted with tetrachloroethylene (3×10 mL), the organic phase pH-adjusted to 4, washed with water (3×10 mL), dried over sodium sulfate and evaporated to dryness. The residue is chromatographed on silicagel [heptanes/AcOEt, 4:1 v:v] giving the title compound [220 mg, 0.39 mmol, 86%] as a pale yellow oil.

$^1$H-NMR (400.1 MHz, CDCl$_3$): δ=1.35 (s, 6H), 3.99 (s, 1H), 5.04-5.10 (3×s, 3×2 H), 5.22-5.30 (3×dd superimposed, 3×1 H), 5.71-5.79 (3×dd superimposed, 3×1 H), 6.65-6.78 (3×dd superimposed, 3×1 H), superimposed with 6.76 (d, 1H), 6.98 (d, 1H), 7.20-7.44 ppm (m, 12H); $^{13}$C-NMR (100.6 MHz, CDCl$_3$): δ=27.3, 70.9, 75.4, 76.7, 78.0, 109.6, 123.3, 126.3, 126.4, 126.5, 127.3, 127.8, 128.9, 129.0, 135.8, 136.0, 136.4, 136.5, 136.6, 137.6, 137.7, 141.4, 150.0, 155.1, 210.4 ppm Example 10: Preparation of 2-hydroxy-2-methyl-1-(4-methylthiophenyl)propan-1-one

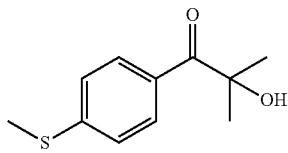

Sodium hydroxide solution (w=50%, 12.35 g, 154.4 mmol) and tetrabutylammonium bromide (0.15 g, 0.46 mmol) were added to a solution of 2-methyl-1-(4-methylthiophenyl)-propan-1-one (3.00 g, 15.4 mmol) and hexachloroethane (5.48 g, 23.16 mmol) in tetrachloroethylene (8 mL). The reaction mixture was stirred at 50° C. for four hours. The resulting solution was taken up with water (20 mL) and the phases were separated. The pH of the aqueous layer was adjusted to 3 with diluted HCl solution. Afterwards, it was extracted with tetrachloroethylene (3×50 mL). The combined organic phases were washed with brine (50 mL), dried over sodium sulfate and the solvent was removed under reduced pressure. The crude product was obtained as a yellow oil (2.96 g, 14.1 mmol, 91% yield).

$^1$H-NMR (400.1 MHz, CDCl$_3$): δ=1.64 (s, 6H), 2.54 (s, 3H), 4.12 (wide s, 1H), 7.26-7.32 (m, 2H), 7.96-8.02 (m, 2H) ppm. $^{13}$C-NMR (100.6 MHz, CDCl$_3$): δ=14.7, 28.6, 76.1, 124.79, 129.4, 130.3, 146.3 ppm.

Example 11: Preparation of 2-methyl-1-(4-methylthiophenyl)-2-morpholino-propan-1-one

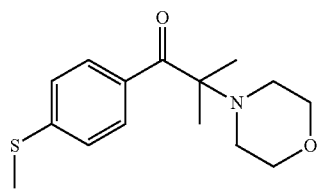 [SMILES: CSc1ccc(C(=O)C(C)(C)N2CCOCC2)cc1]

A mixture of sodium methoxide (30% in methanol, 5.56 g, 30.9 mmol), methanol (5), 2-methyl-1-(4-methylthiophenyl)propan-1-one (1.00 g, 5.14 mmol) and hexachloroethane (1.34 g, 5.66 mmol) was stirred at room temperature for 2 d. Then, methanol was removed from the reaction mixture by distillation under reduced pressure and morpholine (22.4 g, 257 mmol) and sodium hydroxide solution (50%, 4.12 g, 51.5 mmol) were added. The reaction mixture was stirred under reflux for 10 h. Then, the reaction mixture was cooled down to room temperature, the solvent evaporated under reduced pressure and the residue taken up with water (30 mL). The phases were separated and pH of the aqueous layer was adjusted to 1.0 with hydrochloric acid solution (1M). The aqueous layer was extracted with tert-butylmethylether (3×50 mL) to remove impurities. Then the pH of the aqueous layer was adjusted to 14.0 with sodium hydroxide solution (50%) and extracted again with tert-butylmethylether (3×50 mL). The combined organic layers of the second extraction were washed with brine (50 mL), dried over Na$_2$SO$_4$ and the solvent was removed under vacuum. The crude product of 2-methyl-1-(4-methylthiophenyl)-2-morpholino-propan-1-one was obtained as slightly yellowish crystals, (0.91 g, 3.3 mmol, 63% yield).

$^1$H-NMR (400.1 MHz, CDCl$_3$): δ=1.31 (s, 6H), 2.53 (s, 3H), 2.55-2.61 (m, 4H), 3.66-3.73 (m, 4H), 7.20-7.26 (m, 2H), 8.49-8.54 (m, 2H) ppm. $^{13}$C-NMR (100.6 MHz, CDCl$_3$): δ=14.4, 20.4, 47.2, 67.3, 68.3, 124.3, 130.3, 131.8, 144.9, 201.9 ppm. Melting point: 66-68° C.

Example 12: Preparation of 2-ethyl-2-hydroxy-1-phenyl-butan-1-one

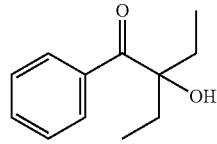

Sodium hydroxide solution (w=50%, 9.08 g, 113 mmol) and tetrabutylammonium hydrogensulfate (0.19 g, 0.57 mmol) were added to a solution of 2-ethyl-1-phenyl-butan-1-one (2.00 g, 11.4 mmol) and hexachloroethane (2.96 g, 12.48 mmol) in tetrachloroethylene (12 mL). The reaction mixture was stirred at 50° C. for 1.5 d. The resulting solution was taken up with water (20 mL) and the phases were separated. The pH of the aqueous layer was adjusted to 3 with dilute HCl solution (1M), and extracted with tetrachloroethylene (3×50 mL). The combined organic phases were washed with brine (50 mL), dried over sodium sulfate and the solvent was removed under reduced pressure. 2-Ethyl-2-hydroxy-1-phenyl-butan-1-one was obtained as a colorless oil (2.09 g, 10.9 mmol, 96% yield).

$^1$H-NMR (400.1 MHz, CDCl$_3$): δ=0.82-0.86 (t, 6H), 1.92-2.04 (m, 2H), 2.06-2.18 (m, 2H), 4.39 (s, 1H), 7.45-7.54 (m, 2H), 7.58-7.65 (m, 1H), 7.97-8.05 (m, 2H) ppm.

Example 13: Preparation of 2-methyl-1-(4-methyl-thiophenyl)-2-morpholino-propan-1-one

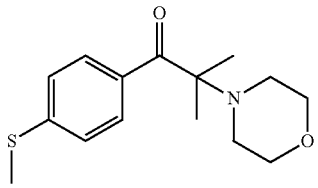 [SMILES: CSc1ccc(C(=O)C(C)(C)N2CCOCC2)cc1]

A mixture of sodium methoxide (30% in methanol, 5.56 g, 30.9 mmol), methanol (5), 2-methyl-1-(4-methylthiophenyl)propan-1-one (1.00 g, 5.14 mmol) and hexachloroethane (1.34 g, 5.66 mmol) was stirred at 40° C. for 24 h. Then, morpholine (22.4 g, 257 mmol) was added and methanol was removed from the reaction mixture by distillation. Afterwards, sodium hydroxide solution (50%, 4.12 g, 51.5 mmol) and tetrabutylammonium hydrogensulfate (0.09 g, 0.27 mmol) were added and the reaction mixture was stirred under reflux for 10 h. Then, the reaction mixture was cooled down to room temperature, the solvent was evaporated under reduced pressure and the residue was taken up with water (30 mL). The phases were separated and the pH of the aqueous layer was adjusted to 7 with saturated ammonium chloride solution. The aqueous layer was extracted with ethyl acetate (3×50 mL). The combined organic layers were washed with brine (50 mL), dried over $Na_2SO_4$ and the solvent was evaporated. The crude product was purified by preparative thin layer chromatography on silica gel [cyclohexane/ethyl acetate, 5:1 v:v]. 2-methyl-1-(4-methylthiophenyl)-2-morpholino-propan-1-one was obtained as a colorless oil (0.95 g, 3.2 mmol, 61% yield).

$^1$H-NMR (400.1 MHz, $CDCl_3$): δ=1.31 (s, 6H), 2.53 (s, 3H), 2.55-2.61 (m, 4H), 3.66-3.73 (m, 4H), 7.20-7.26 (m, 2H), 8.49-8.54 (m, 2H) ppm. $^{13}$C-NMR (100.6 MHz, $CDCl_3$): δ=14.4, 20.4, 47.2, 67.3, 68.3, 124.3, 130.3, 131.8, 144.9, 201.9 ppm.

Example 14: Preparation of 2-methyl-2-morpholino-1-phenylpropan-1-one

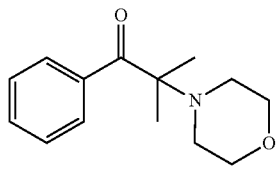 [SMILES: CC(C)(C(=O)c1ccccc1)N1CCOCC1]

A mixture of sodium methoxide (30% in methanol, 22.1 g, 0.410 mol), methanol (30 mL), isobutyrophenone (10.12 g, 68.28 mmol) and hexachloroethane (32.33 g, 136.6 mmol) was stirred at 40° C. for 2 d. Then, further sodium methoxide (30% in methanol, 11.85 g, 0.221 mol) and another equivalent of hexachloroethane (16.2 g, 68.3 mmol) was added and the reaction mixture was stirred at 50° C. for 6 h. Afterwards, methanol was removed from the reaction mixture by distillation under reduced pressure and morpholine (150 g, 1.72 mol) and sodium hydroxide solution (50%, 54.6 g, 0.683 mol) were added. The reaction mixture was stirred overnight at 110° C. Then, it was cooled down to room temperature and slowly poured into conc. hydrochloric acid solution (500 mL). The aqueous layer was separated, the pH was adjusted to 0 by adding further conc. hydrochloric acid solution and then it was extracted with tert-butylmethylether (3×200 mL) to remove impurities. Then, the pH of the aqueous layer was adjusted to 14 with sodium hydroxide solution (50%) and extracted again with tert-butylmethylether (3×200 mL). The combined organic layers of the second extraction were washed with brine (2×100 mL), dried over $Na_2SO_4$ and the solvent was evaporated. The crude product of 2-methyl-2-morpholino-1-phenylpropan-1-one was obtained as red crystals, (7.60 g, 32.6 mmol, 48% yield).

$^1$H-NMR (400.1 MHz, $CDCl_3$): δ=1.34 (s, 6H), 2.57-2.63 (m, 4H), 3.68-3.76 (m, 4H), 7.40-7.46 (m, 2H), 7.50-7.54 (m, 1H), 8.53-8.58 (m, 2H) ppm. $^{13}$C-NMR (100.6 MHz, $CDCl_3$): δ=20.3, 47.1, 67.4, 68.4, 124.9, 130.3, 132.4, 135.9, 203.3 ppm. Melting point: 79-81° C.

Example 15: Preparation of 2-methyl-2-morpholino-1-(4-vinylphenyl)propan-1-one

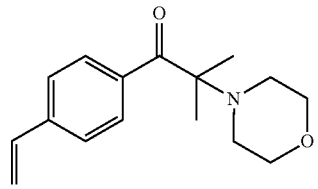 [SMILES: C=Cc1ccc(C(=O)C(C)(C)N2CCOCC2)cc1]

A mixture of sodium methoxide (30% in methanol, 3.72 g, 68.9 mmol), methanol (5 mL), 2-methyl-1-(4-vinylphenyl)propan-1-one (2.00 g, 11.5 mmol) and hexachloroethane (5.45 g, 23.0 mmol) was stirred at 40° C. for 2 d. Then, further sodium methoxide (30% in methanol, 1.85 g, 34.2 mmol) and another equivalent of hexachloroethane (2.75 g, 11.4 mmol) was added and the reaction mixture was stirred at 50° C. for 6 h. Afterwards, methanol was removed from the reaction mixture by distillation under reduced pressure and morpholine (25.0 g, 0.287 mol) and sodium hydroxide solution (50%, 9.18 g, 0.115 mol) were added. The reaction mixture was stirred overnight at 110° C. Then, it was cooled down to room temperature and slowly poured into conc. hydrochloric acid solution (50 mL). The aqueous layer was separated, the pH was adjusted to 0 by adding further conc. hydrochloric acid solution and then it was extracted with tert-butylmethylether (3×20 mL) to remove impurities. Then, the pH of the aqueous layer was adjusted to 14 with sodium hydroxide solution (50%) and extracted again with tert-butylmethylether (3×20 mL). The combined organic layers of the second extraction were washed with brine (2×10 mL), dried over $Na_2SO_4$ and the solvent was evaporated. The crude product was purified by preparative thin layer chromatography on silica gel (c-$C_6H_{12}$:AcOEt=2:1, v:v). 2-methyl-2-morpholino-1-(4-vinylphenyl)propan-1-one was obtained as a colorless oil, (1.78 g, 6.86 mmol, 60% yield).

$^1$H-NMR (400.1 MHz, $CDCl_3$): δ=1.35 (s, 6H), 2.59-2.62 (m, 4H), 3.71-3.73 (m, 4H), 5.39 (dd, 1H), 5.89 (dd, 1H), 6.77 (dd, 1H) 7.42-7.50 (m, 2H), 8.51-8.58 (m, 2H) ppm. $^{13}$C-NMR (100.6 MHz, $CDCl_3$): δ=20.2, 47.1, 67.4, 68.4, 116.3, 125.6, 130.7, 134.9, 136.1, 141.4, 202.6 ppm.

The invention claimed is:
1. A process for the preparation of an α-functionalized ketone of the general formula I,

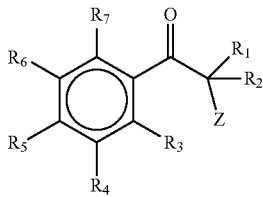

wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, optionally one or more carbon atoms are replaced with O, or two adjacent R form an aromatic system together with the benzene ring of formula I;

Z is selected from $OR_9$, $NHR_9$ and $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O;

the process comprising:
contacting under phase-transfer conditions a ketone of the general formula II

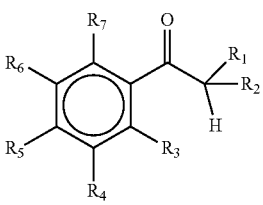

wherein $R_1$, $R_2$, $R_3$, $R_4$, $R_5$, $R_6$ and $R_7$ are as defined above;
with an at least partially halogenated $C_2$-$C_8$-alkane and/or $C_2$-$C_8$-alkene selected from hexachloroethane, tetrachloroethylene and mixtures thereof, and a base selected from the group comprising alkali metal hydroxide, earth alkali metal hydroxide, alkali metal $C_1$-$C_8$-alkoxide, earth alkali metal $C_1$-$C_8$-alkoxide and mixtures thereof, or a base selected from the group comprising alkali metal hydroxide, earth alkali metal hydroxide, alkali metal $C_1$-$C_8$-alkoxide, earth alkali metal $C_1$-$C_8$-alkoxide and mixtures thereof together with the protonated form of Z as defined above, wherein the base is added in form of an aqueous solution or the base is added in an organic solvent selected from the group consisting of methanol, ethanol, n-propanol, tert.-butanol, dichloromethane, tetrachloroethylene, ethyl acetate, acetone, N,N-dimethylformamide, dimethylsulfoxide, 1,2-dimethoxyethane, diethyleneqlycol dimethyl ether, triethyleneglycol dimethyl ether, and mixtures thereof.

2. The process according to claim 1, wherein $R_1$ and $R_2$ are the same.

3. The process according to claim 2, wherein $R_1$ and $R_2$ are selected from H and linear or branched $C_1$-$C_8$-alkyl.

4. The process according to claim 1, wherein $R_1$ and $R_2$ are different and are independently selected from H and linear or branched $C_1$-$C_8$-alkyl.

5. The process according to claim 1, wherein $R_1$ and $R_2$ form $C_4$-$C_{10}$-cycloalkyl together with the connecting C atom.

6. The process according to claim 1, wherein $R_3$, $R_4$, $R_5$, $R_6$ and $R_7$ are the same.

7. The process according to claim 6, wherein $R_3$, $R_4$, $R_5$, $R_6$ and $R_7$ are selected from H and linear or branched $C_1$-$C_8$-alkyl.

8. The process according to claim 1, wherein $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

9. The process according to claim 1, wherein one of $R_3$, $R_4$, $R_5$, $R_6$ and $R_7$ is linear or branched $C_2$-$C_8$-alkenyl, $C_1$-$C_8$-alkoxy, $C_2$-$C_8$-alkenyloxy, $C_9$-$C_{15}$-alkenylarylalkoxy, or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom; and the remaining ones are independently selected from H and linear or branched $C_1$-$C_8$-alkyl.

10. The process according claim 1, wherein two or three of $R_3$, $R_4$, $R_5$, $R_6$ and $R_7$ are linear or branched $C_2$-$C_8$-alkenyl, $C_1$-$C_8$-alkoxy, $C_2$-$C_8$-alkenyloxy, and $C_9$-$C_{15}$-alkenylarylalkoxy, and the remaining ones are independently selected from H and linear or branched $C_1$-$C_8$-alkyl.

11. The process according to claim 1, wherein $R_3$ and $R_4$ or $R_4$ and $R_5$ form an aromatic system together with the benzene ring of formula I.

12. The process according to claim 11, wherein one of the remaining R is linear or branched $C_2$-$C_8$-alkenyl, $C_2$-$C_8$-alkenyloxy, $C_9$-$C_{15}$-alkenylarylalkoxy, and the remaining ones are independently selected from H and linear or branched $C_1$-$C_8$-alkyl.

13. The process according to claim 1, wherein Z is $OR_9$ with $R_9$ being selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy and $C_9$-$C_{15}$-alkenylarylalkoxy or Z is $NR_{10}R_{11}$ with $R_{10}$ and $R_{11}$ being independently selected from H, linear or branched $C_1$-$C_8$-alkyl, $C_3$-$C_8$-cycloalkyl, $C_6$-$C_{14}$-aryl, or $R_{10}$ and $R_{11}$ form a $C_3$-$C_6$-alicyclic system together with the connecting N atom, optionally one or more carbon atoms are replaced with O.

14. The process according claim 1, wherein the base is selected from sodium hydroxide; lithium hydroxide; potassium hydroxide; sodium $C_1$-$C_6$-alkoxide, lithium $C_1$-$C_6$-alkoxide, potassium $C_1$-$C_6$-alkoxide, and mixtures thereof; or the base is selected from sodium $C_1$-$C_6$-alkoxide, potassium $C_1$-$C_6$-alkoxide, together with the protonated form of Z as defined above.

15. The process according to claim 1, wherein the process is carried out at a temperature of at least 30° C.

16. The process according to claim 1, wherein the process is carried out in an organic solvent.

17. The process according to claim 1, wherein the process is carried out in the presence of a phase-transfer catalyst.

18. The process according claim 1, wherein the α-functionalized ketone is obtained in an one-pot reaction.

19. The process according to claim 1, wherein the process further comprises a step of:
   i) separating the obtained organic and aqueous phases, and/or
   ii) extracting the obtained aqueous phase with the organic solvent used in the process and combining the obtained organic phases, and/or
   iii) acidifying the obtained organic phase to a pH of 3 to 6.5.

* * * * *